United States Patent [19]

Nakanishi et al.

[11] 3,988,373

[45] Oct. 26, 1976

[54] QUATERNARY AMMONIUM SALTS

[75] Inventors: Kazuo Nakanishi, Osaka; Takashi Iwata, Kyoto; Hisae Haruta, Ibaraki; Kazuhiko Yoshida; Hideo Yagi, both of Osaka; Akira Hashimoto nee Matui, Suita, all of Japan

[73] Assignee: Fujisawa Pharmaceutical Co., Ltd., Osaka, Japan

[22] Filed: Sept. 16, 1974

[21] Appl. No.: 506,001

Related U.S. Application Data

[63] Continuation-in-part of Ser. No. 127,010, March 22, 1971, Pat. No. 3,850,611.

[30] Foreign Application Priority Data

Mar. 28, 1970 Japan............................ 45-26097
Mar. 28, 1970 Japan............................ 45-26098
Mar. 25, 1970 Japan............................ 45-25544
June 2, 1970 Japan............................ 45-48343
Apr. 6, 1970 Japan............................ 45-29540

[52] U.S. Cl. ............... 260/567.6 M; 260/247.2 R; 260/514 J

[51] Int. Cl.² ...................................... C07C 87/46

[58] Field of Search .................... 260/247, 567.6 M

[56] References Cited

UNITED STATES PATENTS

| | | | |
|---|---|---|---|
| 2,647,122 | 7/1953 | Archer et al. ...................... | 260/247 |
| 2,933,530 | 4/1960 | Kralt et al. ........................ | 260/567.6 M |
| 3,046,280 | 7/1962 | Kralt et al. ........................ | 260/247 |
| 3,109,845 | 11/1963 | Seegar et al. ...................... | 260/247 |

OTHER PUBLICATIONS

Mori et al., Tetrahedron, 1970, 26(11); pp. 2815–2819, (received by Office 8/31/70).
Nakanishi et al., Chem. Abst., 76:24780z, (1972).

Primary Examiner—Lorraine A. Weinberger
Assistant Examiner—Michael Shippen
Attorney, Agent, or Firm—Oblon, Fisher, Spivak, McClelland & Maier

[57] ABSTRACT

A quaternary ammonium salt of the formula:

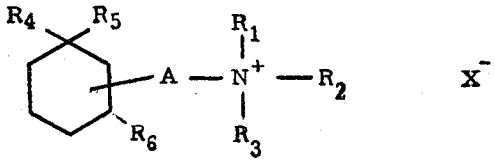

wherein A is a lower alkylene, a lower alkenylene or a lower alkadienylene; $R_1$ and $R_2$ are each lower alkyl which may be linked together directly or by an oxygen atom to form a saturated heterocyclic group; $R_3$ is a lower alkyl, a halo (lower) alkyl, a lower alkynyl, phenyl (lower) alkyl which may have one or more halogen atoms as substituents on the phenyl ring, a lower alkenyl, a hydroxy (lower) alkyl, a carboxy (lower) alkyl or a lower alkenyloxycarbonyl (lower) alkyl; $R_4$, $R_5$ and $R_6$ are each lower alkyl having 1 to 3 carbon atoms; X is an acid residue; and wherein the cyclohexyl ring may have one double bond, with the proviso that when the cyclohexyl ring has one double bond in the 1,2 position, A may not be

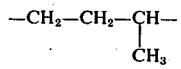

when X⁻ is iodide, $R_4$, $R_5$ and $R_6$ are all methyl; $R_1$, $R_2$ and $R_3$ are all methyl or all ethyl, or $R_1$ is methyl, $R_2$ is ethyl and $R_3$ is phenylisopropyl or isoamyl with the further proviso that when the double bond in the cyclohexyl ring is in the 2,3 position, A may not be

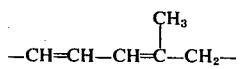

when X⁻ is iodide, and $R_1$, $R_2$, $R_3$, $R_4$, $R_5$ and $R_6$ are all methyl.

1 Claim, No Drawings

QUATERNARY AMMONIUM SALTS

CROSS-REFERENCE TO RELATED APPLICATIONS

This application is a continuation-in-part of U.S. Pat. application Ser. No. 127,010, filed Mar. 22, 1971, now U.S. Pat. No. 3,850,611.

BACKGROUND OF THE INVENTION

Field of the Invention

This invention relates to a new quaternary ammonium salt, a process for preparing the same and a composition of the same useful for regulating plant growth.

Accordingly, the present invention provides, as a novel compound, a quaternary ammonium salt of the formula:

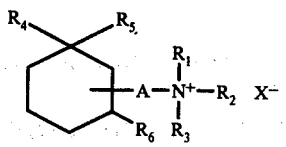
(I)

wherein A is a lower alkylene, a lower alkenylene or a lower alkadienylene; $R_1$ and $R_2$ are each lower alkyl which may be linked together directly or by an oxygen atom to form a saturated hetercyclic group; $R_3$ is a lower alkyl, a halo(lower)alkyl, a lower alkynyl, a phenyl(lower)alkyl which may have one or more halogen atoms as substituents on the phenyl ring, a lower alkenyl, a hydroxy(lower)alkyl, a carboxy(lower)alkyl or a lower alkenyloxycarbonyl(lower)alkyl; $R_4$, $R_5$ and $R_6$ are each lower alkyl having 1 to 3 carbon atoms; X is an acid residue; and a cyclohexyl ring in the above formula may have one double bond.

It is to be understood, within the scope of the present invention, that the term "lower" used in connection with alkyl, alkylene, etc. is intended to mean alkyl, alkylene, etc. having 1 to 10 carbon atoms unless otherwise indicated.

It is further to be understood, in this specification, that the lower alkylene covers methylene, ethylene, isopropylene, propylene, butylene, isobutylene, pentylene, etc.;

the lower alkenylene includes propenylene, 1-methyl-2-propenylene, 2-methyl-2-propenylene, 2-methyl-2-butenylene, etc;

the lower alkaidenylene includes 2,4-pentadienylene, 3-methyl-2,4-pentadienylene, etc.;

the lower alkyl includes methyl, ethyl, propyl, isopropyl, butyl, isobutyl, pentyl, isopentyl, hexyl, heptyl, octyl, etc;

the halo(lower)alkyl includes chloromethyl, bromoethyl, iodomethy., chloroethyl, bromoethyl, iodomethyl, fluoromethyl, fluoroethyl, dichloromethyl, dichloroethyl, dibromomethyl, diiodomethyl, diiodoethyl, chlorobromoethyl, chlorobromopropyl, chloropropyl, bromopropy, iodoisopropyl, etc.;

the lower alkynyl includes ethynyl, 1-propynyl, 2-propynyl-(propargyl), 1-butynyl, 3-methyl-1-butynyl, 1-pentynyl, etc.;

the phenyl(lower)alkyl includes benzyl, phenethyl, 3-phenylpropyl, etc.;

the halogen includes fluorine, chlorine, bromine, bromine, iodine;

the lower alkenyl includes vinyl, 1-propenyl, 2-propenyl-(alkyl), 1-butenyl, 2-butenyl, 3-butenyl, 1-pentenyl, etc;

the hydroxy(lower)alkyl includes hydroxymethyl, 2-hydroxyethyl, 1-hydroxyethyl, 3-hydroxypropyl, 3-hydroxy-2-methylpropyl, 4-hydroxybutyl, 2-hydroxybutyl, etc;

the carboxy(lower)alkyl includes carboxymethyl, 2-carboxyethyl, 3-carboxypropyl, 3-carboxy-2-methylpropyl, 4-carboxybutyl, etc,;

the lower alkenyloxycarbonyl(lower)alkyl includes vinyloxycarbonylmethyl, vinyloxycarbonylethyl, propenyloxycarbonylmethyl, propenyloxycarbonylethyl, allyloxycarbonylmethyl, allyloxycarbonylethyl, allyloxycarbonylpropyl, propenyloxycarbonylpropyl, etc.;

the acid residue includes chloride, iodide, bromide, etc.;

the saturated heterocyclic group includes pyrrolidino, piperidino, morpholino, etc.; and the cyclohexyl ring in the above formula (I) which may have one double bond covers a cyclohexyl ring, for example, having the following formulae:

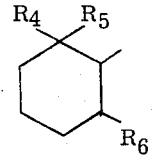 , 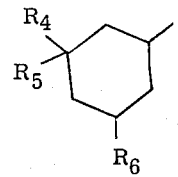

and a cyclohexenyl ring, for example, having the following formulae:

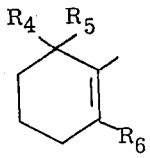 , 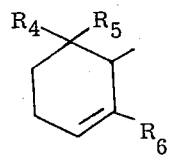

wherein $R_4$, $R_5$ and $R_6$ are each lower alkyl having 1 to 3 carbon atoms.

The quaternary ammonium salt of the formula (I) has a plant growth regulating activity. Specifically, it has a plant growth inhibiting activity due to its anti-gibberellin and anti-auxin action in a plant.

Accordingly, the compounds (I) can be used as growth regulators to artificially control the growth of plants in agriculture and horticulture, and may be useful in various applications typically illustrative as follows:

Use to prevent elongation in the height of plants such as Italian rye grass, orchard grass, sods, etc.;

to prevent lodging of rice plant, wheat, etc. by inhibiting elongation;

to dwarf the height of such vegetables as cucumber, tomato, egg-plant, soybean, peas, kidney bean, Spanish paprike, etc. and flowers such as cosmos, sage, chrysanthemum, cyclamene, poinsettia, stock, morning glory, etc.;

to prevent overgrowth of a pericarp of citrus fruits such as mandarin, orange, etc.;

to inhibit growth of a naught lateral branch of vegetables such as melon, water melon, cucumber, tomato, egg-plant, etc. and fruit trees such as pear, grape, apple, grapefruit, citrus fruits, etc.;

to prevent ear germination of cereals such as rice plant, wheat, etc.;

to accelerate enlargement in the root of edible roots such as radish, yam, onion, sweet potato, potato, chestnuts, carrot, burdock, etc.;

to prevent bolting of vegetables such as cabbage, white rape, carrot, radish, spinach, burdock, etc.;

to alleviate frost damage, damage from a drought, damage from a salty wind or damage from a hotness, of fruits such as Japanese persimmon, grape, mulberry, etc. and vegetables such as green pea, spinach, lettuce, etc.;

to accelerate ripeness of fruits such as mandarin, apple, peach, grape, tomato, cherry, strawberry, etc.;

to accelerate female flower bud formation of cucumber, water melon, melon, pumpkin, etc.;

to induce flower-bud formation of flowers such as morning glory, cosmos, salvia, potmum, etc. and fruits such as apple, peach, grape, persimmon, etc.

The compound (I) may be further expected to be useful in various applications as follows:

Use to prevent head cracking of globose vegetables such as cabbage, etc.;

to prevent cracking of fruits such as grape, cherry, apple, etc.;

to prevent overripening of water melon, melon, etc.;

to prevent sprouting of plants such as potato, sweet potato, yam onion, chestnuts, etc. during storage thereof;

to prevent generation and growth of auxilliary buds of tobacco plant, particularly after pinching of terminal bud;

to improve storageability of cereals such as rice, wheat, corn, etc., fruits such as apple, chestnuts, etc., vegetables such as onion, yam, potato, sweet potato, etc., and other seeds or crops;

to prevent malformation of egg-plants caused by side effect of some agricultural chemicals;

to accelerate a vernalization, as control of a flower-bud formation, of plants such as grape, mandarin, apple, peach, barley, rye, wheat, etc.;

to prevent dropping of fruits such as apple, mandarin, peach, pear, etc.

SUMMARY OF THE INVENTION

This invention provides the quaternary ammonium salt of the formula:

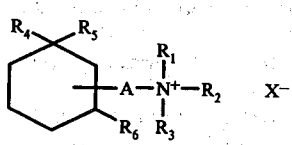

wherein A is a lower alkylene, a lower alkenylene or a lower alkadienylene; $R_1$ and $R_2$ are each lower alkyl which may be linked together directly or by an oxygen atom to form a saturated heterocyclic group; $R_3$ is a lower alkyl, a halo(lower)alkyl, a lower alkynyl, phenyl(lower)alkyl which may have one or more halogen atoms as substituents on the phenyl ring, a lower alkenyl, a hydroxy(lower)alkyl, a carboxy(lower)alkyl or a lower alkenyloxycarbonyl(lower)alkyl; $R_4$, $R_5$ and $R_6$ are each lower alkyl having 1 to 3 carbon atoms; X is an acid residue; and wherein the cyclohexyl ring may have one double bond with the proviso that when the cyclohexyl ring has one double bond in the 1,2 position, A may not be

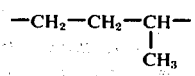

wherein $X^-$ is iodide, $R_4$, $R_5$ and $R_6$ are all methyl; $R_1$, $R_2$ and $R_3$ are all methyl or all ethyl, or $R_1$ is methyl, $R_2$ is ethyl and $R_3$ is phenylisopropyl or isoamyl, with the further proviso that when the double bond in the cyclohexyl ring is in the 2,3 position, A may not be

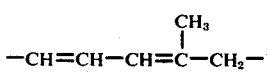

wherein $X^-$ is iodide, and $R_1$, $R_2$, $R_3$, $R_4$, $R_5$ and $R_6$ are all methyl.

DETAILED DESCRIPTION OF THE PREFERRED EMBODIMENTS

The compound (I) of this invention is prepared by reaction of a tertiary amine of the formula:

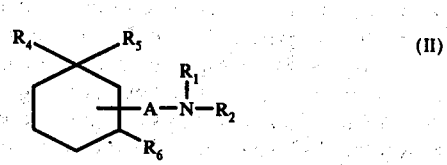

wherein A, $R_1$, $R_2$, $R_4$, $R_5$ and $R_6$ are the same as defined above; and a cyclohexyl ring in the above formula may have one double bond with a compound of the formula:

wherein $R_3$ is the same as defined above and X' is an acid residue, in the presence or absence of a metal acid addition salt.

The starting tertiary amine of the formula (II) to be used in this reaction is partly known, e.g. [1-methyl-3-(2,6,6-trimethyl-1-cyclohexenyl)propyl]dimethylamine [Chemical Abstracts, volume 56, column 876b]; and [1-methyl-3-(2,6,6-trimethylcyclohexyl)propyl]dimethylamine [Chemical Abstracts, volume 58, column 8933e].

Further, the starting tertiary amine of the formula (II) can be prepared by the following methods.

a. A tertiary amine of the formula:

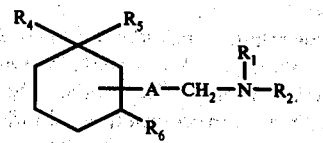

wherein A is a lower alkylene, a lower alkenylene or a lower alkadienylene; $R_1$ and $R_2$ are each lower alkyl, which may be linked together directly or by an oxygen atom to form a saturated heterocyclic group; $R_4$, $R_5$ and $R_6$ are each lower alkyl having 1 to 3 carbon atoms; and the cyclohexyl ring in the above formula may have one double bond, with the above provisos, is prepared by reacting a compound of the formula:

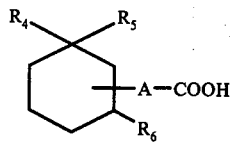

wherein A, $R_4$, $R_5$ and $R_6$ are the same as defined above; and the cyclohexyl ring in the above formula may have one double bond, or its reactive derivative at the carboxyl group, with an amine of the formula:

wherein $R_1$ and $R_2$ are the same as defined above, and then reducing the resulting compound of the formula:

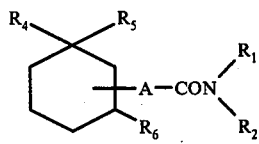

wherein A, $R_1$, $R_2$, $R_4$, $R_5$ and $R_6$ are the same as defined above; and a cyclohexyl ring in the above formula may have one double bond with a reducing agent selected from an alkali metal boron hydride, an alkali metal lithium hydride, and a combination of alkali metal and alcohol.

b. A tertiary amine of the formula:

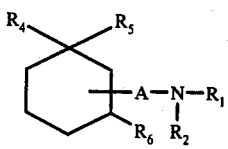

wherein A is a lower alkylene, a lower alkenylene or a lower alkadienylene; $R_1$ and $R_2$ are each lower alkyl which may be linked together directly or by an oxygen atom to form a saturated heterocyclic group; $R_4$, $R_5$ and $R_6$ are each lower alkyl having 1 to 3 carbon atoms; and the cyclohexyl ring in the above formula may have one double bond, with the above provisos, is prepared by reacting a compound of the formula:

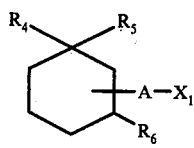

wherein A, $R_4$, $R_5$ and $R_6$ are the same as defined above; $X_1$ is an acid residue; and the cyclohexyl ring in the above formula may have one double bond, with an amine of the formula:

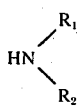

wherein $R_1$ and $R_2$ are the same as defined above.

c. A tertiary amine of the formula:

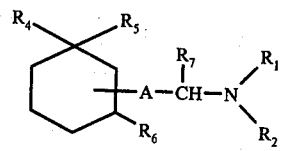

wherein A is a lower alkylene, a lower alkenylene or a lower alkadienylene; $R_1$ and $R_2$ are each lower alkyl which may be linked together directly or by an oxygen atom to form a saturated heterocyclic group; $R_4$, $R_5$ and $R_6$ are each lower alkyl having 1 to 3 carbon atoms; $R_7$ is a hydrogen or a lower alkyl; and the cyclohexyl ring in the above formula may have one double bond with the above provisos, is prepared by reacting formic acid and an amine of the formula:

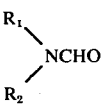

wherein $R_1$ and $R_2$ are the same as defined above, with a compound of the formula:

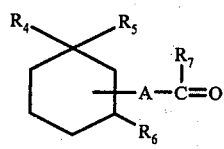

wherein A, $R_4$, $R_5$, $R_6$ and $R_7$ are the same as defined above; and the cyclohexyl ring in the above formula may have one double bond; with the above provisos.

The reaction for preparing a compound of the formula (I) is ordinarily carried out in the absence of a solvent, but, if necessary, it may be also carried out in an inert solvent. Examples of the said solvent are methanol, ethanol, ether, benzene, etc. When the present reaction is carried out in the presence of a metal acid addition salt, such as sodium chloride, potassium chloride, sodium bromide, potassium bromide, sodium iodide, potassium iodide, silver chloride, silver bromide, silver iodide, etc., a quaternary ammonium salt (I) having an acid residue of the metal acid addition salt instead of an acid residue of a compound (III) may be obtained. When the reaction is carried out in the presence of sodium iodide, potassium iodide or the like, such compound may promote the present reaction. There is no limitation as to the reaction temperature.

The quaternary ammonium salt (I) of the present invention is rarely applied directly onto plants, and used in the form of compositions comprising at least one of the quaternary ammonium salt of the formula (I) in association with a carrier, or a surface-active agent, or both a carrier and a surface-active agent. The effectiveness of the compound of the present invention, when the compound is used as plant growth regulators, will depend on the concentration applied. Considerable ranges of an effective concentration of the quaternary ammonium salt (I) as plant growth regulators will be observed depending not only on the kind, organ or texture of plants to be treated, but also on the physiological age of the plants. Thus, the concentration to be employed should be determined suitably depending on the intended use of the agent, the type of plants to be treated and the period of application. Usually, the effective concentration, however, will be within the range of 1–5000 ppm and preferably of 10–500 ppm, although these are not critical.

Now the plant growth regulating activity of typical compounds which fall within the category of the compound of the formula (I) of this invention is illustrated by reference to various tests in which individual active ingredients are the following numbered compounds.

Compound No. 1

[3-methyl-5-(2,6,6-trimethyl-1-cyclohexenyl)-2,4-pentadienyl]trimethylammonium iodide Compound No. 2

[1-methyl-3-(2,6,6-trimethyl-2-cyclohexenyl)-2-propenyl]trimethylammonium iodide Compound No. 3

[1-methyl-3-(2,6,6-trimethyl-1-cyclohexenyl)-propyl]trimethylammonium iodide

Compound No. 4

[3-(2,6,6-trimethyl-1-cyclohexenyl)-2-propenyl]-trimethylammonium iodide

Compound No. 5

[1-methyl-3-(2,6,6-trimethylcyclohexyl)propyl]-trimethylammonium iodide

Compound No. 6

[1-methyl-3-(2,6,6-trimethyl-2-cyclohexenyl)-2-propenyl]dimethylpropylammonium iodide Compound No. 7

[1-methyl-3-(2,6,6-trimethyl-2-cyclohexenyl)-2-propenyl]dimethylethylammonium iodide Compound No. 8

[1-methyl-3-(2,6,6-trimethylcyclohexyl)propyl]-trimethylammonium bromide

Compound No. 9

[1-methyl-3-(2,6,6-trimethyl-2-cyclohexenyl)-2-propenyl]trimethylammonium chloride Compound No. 10

[1-methyl-3-(2,6,6-trimethyl-2-cyclohexenyl)-2-propenyl]trimethylammonium bromide Compound No. 11

[1-methyl-3-(2,6,6-trimethylcyclohexyl)propyl]-dimethyl(3,4-dichlorobenzyl)ammonium iodide Compound No. 12

4-methyl-4-[1-methyl-3-(2,6,6-trimethyl-2-cyclohexenyl)-2-propenyl]morpholinium iodide Compound No. 13

[1-methyl-3-(2,6,6-trimethyl-2-cyclohexenyl)-2-propenyl]dimethylpropargylammonium iodide Compound No. 14

[1-methyl-3-(2,6,6-trimethyl-2-cyclohexenyl)-2-propenyl]dimethylheptylammonium iodide Compound No. 15

1-methyl-[1-methyl-3-(2,6,6-trimethyl-2-cyclohexenyl)-2-propenyl]piperidinium iodide Compound No. 16

[1-methyl-3-(2,6,6-trimethyl-2-cyclohexenyl)-2-propenyl]dimethyl(2-propenyl)ammonium iodide Compound No. 17

[1-methyl-3-(2,6,6-trimethyl-2-cyclohexenyl)-2-propenyl]dimethyl(2-hydroxyethyl)ammonium iodide Compound No. 18

[1-methyl-3-(2,6,6-trimethyl-1-cyclohexenyl)-2-propenyl]trimethylammonium chloride Compound No. 19

[1-methyl-3-(2,6,6-trimethyl-2-cyclohexenyl)-2-propenyl]dimethyl(2,4-dichlorobenzyl)ammonium iodide Compound No. 20

[1-methyl-3-(2,6,6-trimethyl-1-cyclohexenyl)-2-propenyl]dimethyl(2,4-dichlorobenzyl)ammonium iodide Compound No. 21

[1-methyl-3-(2,6,6-trimethyl-1-cyclohexenyl)-2-propenyl]dimethylheptylammonium iodide Compound No. 22

[1-methyl-3-(2,6,6-trimethyl-2-cyclohexenyl)-2-propenyl]dimethylheptylammonium iodide Compound No. 23

[1-methyl-3-(2,6,6-trimethyl-1-cyclohexenyl)-2-propenyl]dimethyl(3,4-dichlorobenzyl)ammonium iodide Compound No. 24

[1-methyl-3-(2,6,6-trimethyl-2-cyclohexenyl)-2-propenyl]dimethyl(3,4-dichlorobenzyl)ammonium iodide Compound No. 25

[1-methyl-3-(2,6,6-trimethyl-1-cyclohexenyl)-2-propenyl]dimethyl(4-chlorobenzyl)ammonium iodide

Compound No. 26

[1-methyl-3-(2,6,6-trimethyl-2-cyclohexenyl)-2-propenyl]dimethyl(4-chlorobenzyl)ammonium iodide

Compound No. 27

[1-methyl-3-(2,6,6-trimethyl-2-cyclohexenyl)-2-propenyl]dimethyl(4-chlorobenzyl)ammonium chloride

Compound No. 28

[1-methyl-3-(2,6,6-trimethylcyclohexyl)propyl]-dimethyl(2,4-dichlorobenzyl)ammonium chloride

Compound No. 29

[1-methyl-3-(2,6,6-trimethyl-2-cyclohexenyl)-2-propenyl]dimethyl(3,4-dichlrobenzyl)ammonium bromide

Compound No. 30

[1-methyl-3-(2,6,6-trimethyl-2-cyclohexenyl)-2-propenyl]dimethyl(2-carboxyethyl)ammonium iodide

Compound No. 31

[1-methyl-3-(2,6,6-trimethyl-2-cyclohexenyl)-2-propenyl]dimethyl(2-propenyloxycarbonylmethyl)ammonium iodide

Compound No. 32

[1-methyl-3-(2,6,6-trimethylcyclohexyl)propyl]-dimethylpropargylammonium iodide

Compound No. 33

[1-methyl-3-(2,6,6-trimethyl-2-cyclohexenyl)-2-propenyl]dimethyl(2-bromoethyl)ammonium bromide

Compound No. 34

[1-methyl-3-(2,6,6-trimethyl-2-cyclohexenyl)-2-propenyl]dimethyl(2-bromoethyl)ammonium iodide

Compound No. 35

[1-methyl-3-(2,6,6-trimethyl-2-cyclohexenyl)-2-propenyl]dimethyl(3,4-dichlorobenzyl)ammonium bromide.

TEST 1

Ten ml. of an aqueous solution of the test compound mentioned below with a specified concentration was poured into a glass tube of 10 cm. length and 3 cm. diameter. Ten rice seeds germinating slightly were placed therein and were allowed to grow for 6 days at 25° ± 1° C under a 300-lux light preventing the evaporation of water. Then, the length of the second leaf sheath was measured. The results are set forth in the following table, in which the elongation ratio (%) is expressed as a relative value when the elongation of control plant in the non-treatment area is rated as 100.

| Compound No. | Concentration (ppm) | | | | |
|---|---|---|---|---|---|
| | 200 | 100 | 50 | 10 | 1 |
| 1 | 16 | 54 | 73 | 87 | 115 |
| 2 | 0 | 35 | 48 | 76 | 86 |
| 3 | 42 | 44 | 59 | 88 | 82 |
| 4 | 29 | 58 | 61 | 83 | 86 |
| 5 | 0 | 57 | 62 | 86 | 100 |
| 6 | 0 | 53 | 63 | 100 | 95 |
| 7 | 0 | 53 | 68 | 89 | 95 |
| 11 | 0 | 0 | 67 | 87 | 100 |
| 16 | 0 | 72 | 97 | 98 | 101 |
| 9 + 18* | 29 | 46 | 73 | — | 99 |
| 8 | — | 28 | 54 | 75 | 80 |
| 10 | — | 82 | 93 | — | — |
| 12 | — | 34 | 59 | 79 | 83 |
| 13 | — | 31 | 60 | 83 | 89 |
| 14 | — | 42 | 53 | 62 | 64 |
| 15 | — | 20 | 43 | 63 | 67 |
| 17 | — | 54 | 67 | 77 | 79 |
| 19 | — | 79 | 89 | — | — |
| 21 + 22* | — | 34 | 56 | 74 | 78 |
| 23 + 24* | — | 54 | 63 | 71 | 72 |
| 25 + 26* | — | 62 | 70 | 76 | 78 |
| 27 | — | 82 | 88 | 93 | 94 |
| 28 | — | 40 | 62 | 79 | 83 |
| 29 | — | 61 | 73 | 82 | 84 |
| 31 | — | 56 | 69 | 79 | 81 |
| 32 | — | 57 | 70 | 81 | 83 |
| 34 | — | 64 | 88 | — | — |
| 35 | — | 43 | 67 | 86 | 90 |

*Note: The solution contains the two kind of compounds at the equivalent amount.

TEST 2

Five ml. of an aqueous solution of the test compound mentioned below with a specified concentration was poured into a glass tube of 10-cm. length and 3-cm. diameter, and an aqueous solution of gibberellin (20 ppm) was added thereto. Ten rice seeds germinating slightly were treated in a similar manner to Test 1, and the length of the second leaf sheath was measured. The results are set forth in the following table, in which the elongation ratio (%) is expressed as a relative value when the elongation of the control plant which was treated with gibberellin (20 ppm) alone is rated as 100.

| Compound No. | Concentration (ppm) | | | | |
|---|---|---|---|---|---|
| | 200 | 100 | 50 | 10 | 1 |
| 1 | 20 | 23 | 34 | 78 | 80 |
| 2 | 0 | 31 | 54 | 91 | 96 |
| 3 | 31 | 41 | 69 | 96 | 100 |
| 5 | 0 | 16 | 23 | 69 | 90 |
| 6 | 0 | 49 | 54 | 97 | 115 |
| 7 | 39 | 56 | 80 | 111 | 120 |
| 11 | 21 | 23 | 45 | 61 | 89 |
| 16 | 16 | 35 | 78 | 81 | 100 |
| 9 + 18* | 13 | 34 | 46 | 73 | 83 |
| 19 + 20* | 24 | 35 | 46 | 76 | 75 |

*Note: The solution contains the two kinds of compounds at the equivalent amount.

TEST 3

Five ml. of an aqueous solution of the test compound mentioned below with a specified concentration was poured into a petri dish of 7-cm, diameter having a filter paper at the bottom. Ten seeds each of rice and Panicum sp. were placed in each of two petri dishes, and were allowed to grow under a 300-lux light for 10 days at 24° C. Then the height of plant and length of the root were measured respectively. The results are set forth in the following table, wherein the root length and height of the plants are expressed as a relative value (%) when those of the control plants in the non-treatment area are rated as 100.

| Compound No. | Conc. (ppm) | Rice | | Panicum sp. | |
|---|---|---|---|---|---|
| | | Root length | Height | Root length | Height |
| | 100 | 13 | 42 | 3 | 72 |
| 5 | 20 | 65 | 57 | 50 | 111 |

-continued

| Compound No. | Conc. (ppm) | Rice Root length | Height | Panicum sp. Root length | Height |
|---|---|---|---|---|---|
| | 4 | 86 | 83 | 120 | 130 |
| 6 | 100 | 19 | 57 | 10 | 66 |
| | 20 | 52 | 64 | 63 | 108 |
| | 4 | 95 | 110 | 103 | 111 |
| 7 | 100 | 11 | 28 | 17 | 62 |
| | 20 | 43 | 40 | 77 | 90 |
| | 4 | 76 | 77 | 150 | 111 |
| 12 | 100 | 14 | 30 | 27 | 11 |
| | 20 | 43 | 83 | 67 | 111 |
| | 4 | 103 | 89 | 83 | 136 |
| 15 | 100 | 6 | 43 | 0 | 36 |
| | 20 | 21 | 51 | 20 | 75 |
| | 4 | 54 | 66 | 100 | 126 |
| 2 | 100 | 13 | 51 | 7 | 45 |
| | 20 | 54 | 57 | 40 | 96 |
| | 4 | 67 | 58 | 83 | 100 |

TEST 4

Five ml. of an aqueous solution of the test compound mentioned below with a specified concentration was poured into a petri dish of 9-cm. diameter having a filter paper at the bottom. Seven seeds of cucumber were placed therein, and were kept at 30° C. for 48 hours. The seeds were further allowed to grow for 10 days at 24° ± 1° C. under a 300-lux light. The length of the hypocotyl was measured. The results are set forth in the following table, wherein the elongation ratio (%) is expressed as a relative value when the elongation of the control plant is rat rated as 100.

| Compound No. | Concentration (ppm) | | | | |
|---|---|---|---|---|---|
| | 200 | 100 | 50 | 20 | 2 |
| 2 | 15 | 16 | 23 | 52 | 48 |
| 3 | 9 | 21 | 24 | 47 | 35 |
| 4 | 13 | 24 | 21 | 43 | 50 |
| 5 | 5 | 5 | 51 | 59 | 81 |
| 6 | 3 | 22 | 51 | 59 | 73 |
| 7 | 14 | 35 | 57 | 59 | 78 |
| 10 | 30 | 54 | 68 | 74 | 89 |
| 12 | 49 | 59 | — | 73 | 81 |
| 15 | 23 | 36 | 49 | 54 | 69 |

TEST 5

Seeds of cucumber were sowed in a porous pot. When the average length of foliage leaves became 1.5 cm., the length from the base of copyledon up to the growth point was measured — this length is referred to as a symbol "A" in the table — and an aqueous solution of the test compound mentioned below with a specified concentration was sprayed onto leaves. Ten days after, the length from the base of copyledon up to the growth point — this length is referred to as a symbol "B" in the table — and the same test solution as mentioned above sprayed again. After a lapse of an additional 20 days, the length from the base of copyledon up to the growth point was measured — this length will hereinafter be referred to by a symbol "C" in the table. Values of B/A and C/B were calculated for each compound. The same calculation as mentioned above was also conducted for the control in which the plants were not treated with the test compound. The figure in the table means the percent (%) of the calculated value or — the treatment area to the calculated one on the control. The results are set forth in the following table.

| Compound No. | Concentration (ppm) | | | |
|---|---|---|---|---|
| | 500 | | 200 | |
| | B/A | C/B | B/A | C/B |
| 3 | 72 | 89 | 84 | 100 |
| 4 | 78 | 95 | 93 | 100 |
| 6 | 94 | 100 | 84 | 95 |
| 8 | 66 | 84 | 81 | 95 |
| 9 | 78 | 95 | 81 | 95 |
| 10 | 75 | 89 | 81 | 95 |
| 13 | 81 | 100 | 88 | 95 |

TEST 6

Cucumber seeds were sowed in a flowerpot of 10 cm. diameter. When the number of foliage leaves is 1.5 in. average, an aqueous solution of the test compound mentioned below with a specified concentration was sprayed onto the leaves. When the average number of foliage leaves was 3, the solution mentioned above was sprayed again. Fifty days after sowing, the height up to the 15th node, the number of leaves, the overall height of the plants and the average internode distance were measured. The results are set forth in the following table, wherein the growth ratio (%) is expressed as a relative value to the control plants in the non-treatment area.

| Compound No. | Conc (ppm) | Height up to 15th node | Height of plant | No. of leaf | Average internode distance |
|---|---|---|---|---|---|
| | 100 | 50.1 | 35.8 | 72.0 | 49.6 |
| | 50 | 52.2 | 36.5 | 68.0 | 53.7 |
| 2 | 10 | 93.2 | 73.3 | 84.0 | 87.4 |
| | 1 | 91.2 | 84.8 | 96.0 | 88.3 |
| | 100 | 79.1 | 67.3 | 88.0 | 76.6 |
| | 50 | 74.8 | 63.4 | 86.0 | 93.6 |
| 3 | 10 | 108.8 | 97.2 | 96.0 | 100.9 |
| | 1 | 97.1 | 85.5 | 93.2 | 93.0 |
| | 100 | 72.0 | 55.8 | 80.0 | 69.5 |
| | 50 | 90.0 | 71.7 | 84.0 | 85.3 |
| 4 | 10 | 108.8 | 96.6 | 89.2 | 107.9 |
| | 1 | 106.1 | 93.1 | 90.0 | 103.2 |

TEST 7

Slightly germinating seeds of Pisum sp. were sowed in a flowerpot of 10 cm. diameter. After a lapse of 15 days, the length from the base of the scaly leaf to the growth point was measured — this length will hereinafter be referred to by the symbol "A" — and an aqueous solution of the compound mentioned below with a specified concentration was sprayed onto the leaves. Seven days thereafter, the length from the base of the scaly leaf to the growth point was measured — this length will hereinafter be referred to by the symbol "B" — and the test solution as mentioned above was sprayed again. Seven days afterwards, the length from the base of the scaly leaf to the growth point was measured — this length will hereinafter be referred to by a symbol "C". Values of B/A, C/A and C/B were calculated for each compound. The same calculation as mentioned above was conducted for the control in which the plants were not treated with the test compound. The figure in the table means the percent (%) of the calculated value on the treatment area to the calculated one on the control. The results are set forth in the following table.

| Compound No. | Concentration (ppm) 500 | | | Concentration (ppm) 100 | | |
| --- | --- | --- | --- | --- | --- | --- |
| | B/A | C/A | C/B | B/A | C/A | C/B |
| 4 | 87 | 76 | 87 | 91 | 91 | 100 |
| 5 | 87 | 79 | 87 | 74 | 85 | 107 |
| 11 | 83 | 79 | 93 | 87 | 82 | 93 |
| 14 | 78 | 71 | 87 | 109 | 97 | 87 |

TEST 8

Five ml. of an aqueous solution of the compound mentioned below with a specified concentration was poured into a petri dish of 9-cm. diameter having filter paper at the bottom. Seeds of tomato were placed therein and, after being kept at 30° C. for 48 hours, were allowed to grow under a 300-lux light for 10 days at 24° ± 1° C. The length of the hypocotyl was measured. The results are set forth in the following table, wherein the elongation ratio (%) is expressed as a relative value to the control.

| Compound No. | Concentration (ppm) | | | | |
| --- | --- | --- | --- | --- | --- |
| | 200 | 100 | 50 | 10 | 1 |
| 2 | 30.2 | 56.2 | 69.2 | 79.6 | — |
| 4 | 0 | 33.4 | 57.9 | 77.5 | — |
| 13 | 6.5 | 44.5 | 62.5 | 78.7 | — |
| 17 | 47.9 | 64.9 | 73.4 | 80.2 | — |
| 5 | — | 61 | 75 | 86 | 88 |
| 7 | — | 49 | 67 | 82 | 85 |
| 8 | — | 39 | 59 | 74 | 78 |
| 15 | — | 40 | 56 | 68 | 71 |
| 23 + 24* | — | 48 | 70 | 87 | 91 |
| 29 | — | 47 | 73 | 94 | — |
| 30 | — | 47 | 71 | 90 | — |
| 31 | — | 62 | 78 | 90 | 93 |
| 32 | — | 3 | 45 | 78 | 86 |

(*Note: The test solution contains two kinds of the compounds at the equivalent amount.)

TEST 9

Seeds of cucumber were allowed to grow under the same conditions as shown in the Test 1 except for using an aqueous solution of the compound mentioned below with a specified concentration. The length of the hypocotyl was measured. The results are set forth in the following table, wherein the elongation ratio (%) is expressed as a relative value to the control.

| Compound No. | Concentration (ppm) | | | |
| --- | --- | --- | --- | --- |
| | 100 | 50 | 10 | 1 |
| 11 | 32 | 56 | 75 | 79 |
| 13 | 29 | 50 | 64 | 69 |
| 17 | 38 | 46 | 50 | 53 |
| 23 + 24* | 48 | 68 | 80 | 88 |
| 25 + 26* | 54 | 70 | 80 | 86 |
| 29 | 59 | 75 | 85 | 91 |
| 30 | 53 | 66 | 77 | 79 |
| 31 | 36 | 61 | 82 | 86 |
| 32 | 0 | 22 | 83 | — |
| 33 | 28 | 47 | 63 | 66 |

| Compound No. | Concentration (ppm) | | | |
| --- | --- | --- | --- | --- |
| | 100 | 50 | 10 | 1 |
| 34 | 8 | 41 | 67 | 73 |

(*Note: The test solution contains two kinds of compounds at the equivalent amount.)

TEST 10

Seeds of cucumber were sowed in mid-January. Thirty-four days after, seedlings were transplanted in a greenhouse. When the plants had ten foliage leaves in average, i.e., 19 days after transplantation, an aqueous solution of the test compound No. 2 with a concentration of 25 ppm was sprayed onto the leaves. Twenty two days after spraying, the height of plants was measured. After the plants were further grown, the total yield (g) of cucumbers harvested 125 days after sowing was weighed. The results are shown as follows:

| Compound No. | Height (cm) | Yield (g) |
| --- | --- | --- |
| 2 | 118 | 11,920 |
| Control | 133 | 9,690 |

TEST 11

Seeds of cucumber were sowed in mid-December. When the plants had 2 leaves on the average, i.e., 27 days after sowing, an aqueous solution of the test compound with a specified concentration was sprayed onto the leaves. Thirty seven days after sowing, seedlings were transplanted to a greenhouse. After 105 days, the internode lengths between the 1st node and the 15th one, between the 1st node and the 30th one and between the 1st node and the upper one, respectively, were measured. At the same time, the total number of nodes, female flowers and fructifying branches were counted, and then the states of yield were examined. The results are set forth in the following tables.

(A) Internode lengths

| Compound No. | Conc. (ppm) | <15th node (%) | <30th node (%) | >30th node (%) | Total numbers node's (%) |
| --- | --- | --- | --- | --- | --- |
| 2 | 50 | 75.4 | 88.0 | 87.5 | 84.7 |
| | 100 | 79.1 | 85.8 | 84.9 | 82.6 |
| 4 | 50 | 88.9 | 93.3 | 92.6 | 89.3 |
| | 100 | 79.1 | 85.4 | 84.6 | 85.7 |
| 5 | 50 | 66.2 | 79.2 | 78.4 | 81.6 |
| | 100 | 53.0 | 73.4 | 71.6 | 75.4 |
| 9 | 50 | 71.6 | 84.3 | 83.3 | 83.7 |
| | 100 | 59.3 | 76.0 | 75.0 | 79.8 |
| Control (Non-treatment) | — | 149.3 cm (100) | 276.6 cm (100) | 295.1 cm (100) | 48.4 (100) |

Note: The figure means a relative value (%) to the control.

(b) Ratio of female flower Number and the states of yield:

| Compound No. | Conc. (ppm) | 1st-10th node A | 1st-10th node B | 11th-20th node A | 11th-20th node B | 21th-30th node A | 21th-30th node B | Number of branch bearing fruits | The position of node bearing the first female flower |
| --- | --- | --- | --- | --- | --- | --- | --- | --- | --- |
| | 50 | 45 | 42 | 92 | 70 | 98 | 88 | 6.7 | 3.5 |

-continued

|   | | | | | | | | | |
|---|---|---|---|---|---|---|---|---|---|
| 2 | 100 | 43 | 37 | 93 | 77 | 98 | 92 | 10.0 | 3.8 |
|   | 50 | 43 | 42 | 85 | 65 | 93 | 83 | 13.0 | 3.7 |
| 4 | 100 | 33 | 22 | 92 | 50 | 92 | 75 | 8.3 | 5.8 |
|   | 50 | 35 | 32 | 93 | 52 | 98 | 87 | 3.3 | 5.8 |
| 5 | 100 | 35 | 25 | 98 | 62 | 95 | 77 | 12.0 | 4.2 |
|   | 50 | 35 | 30 | 87 | 58 | 98 | 92 | 8.3 | 5.0 |
| 9 | 100 | 28 | 20 | 90 | 63 | 100 | 87 | 3.3 | 6.5 |
| Control (Non-treatment) | — | 32 | 28 | 72 | 62 | 88 | 75 | 4.2 | 4.8 |

Note:
In the above table, A refers to "ratio of female flower number" which is calculated from the following formula:

$$A = \frac{\text{Number of female flower}}{\text{Number of node}} \times 100$$

and B refers to "fructification percent per one node" which is calculated from the following formula:

$$A = \frac{\text{Number of fructification}}{\text{Number of node}} \times 100$$

TEST 12

Seeds of tomato were sowed at the end of October. When the plants had 6 foliage leaves on the average, i.e., 48 days after sowing, an aqueous solution of the compound mentioned below with a specified concentration was sprayed onto the plants. Twenty five days after spraying, seedlings were transplanted into a greenhouse. The following items were observed on the specified day as given in the table.

(A) Observation of growth 5 days after transplantation.

| Compound No. | Conc. (ppm) | Height | The position of node bearing the first flower cluster |
|---|---|---|---|
| 2 | 10 | 32.3(81.6) | 8.1 |
|   | 25 | 32.9(83.1) | 8.3 |
| Control | — | 39.6(100) | 8.4 |

(Note: The figure in parenthesis means a relative value (%) to the control.)

(B) States of yield during 138 days after transplantation.

| Compound No. | Conc. (ppm) | No. of fruit harvested | | |
|---|---|---|---|---|
| | | 1st fruit cluster | 2nd fruit cluster | 3rd fruit cluster |
| 2 | 10 | 3.8 | 1.2 | 3.0 |
|   | 25 | 5.0 | 2.0 | 1.4 |
| Control | — | 3.6 | 1.2 | 0 |

| Compound No. | Conc. (ppm) | Average weight of fruit (g) | | |
|---|---|---|---|---|
| | | 1st fruit cluster | 2nd fruit cluster | 3rd fruit cluster |
| 2 | 10 | 132 | 197 | 115 |
|   | 25 | 114 | 158 | 128 |
| Control | — | 143 | 110 | 90 |

TEST 13

Seeds of tomato were sowed in mid-December, and 45 days afterwards, an aqueous solution of Compound No. 19 (200 ppm) was sprayed onto the plant having six foliage leaves. Seedlings were transplanted to a greenhouse. Fifteen days after transplantation, the plants were allowed to grow by means of a gravel culture provided with underground heating facilities, and the yield in both weight and number of fruits harvested during subsequent 124 days was observed.

| Compound No. | Conc. (ppm) | Total No. of fruit | Total weight (kg) | Average weight per fruit (g) |
|---|---|---|---|---|
| 19 | 200 | 12.45 | 1.86 | 149 |
| Control | — | 10.83 | 1.52 | 140 |

TEST 14

Seeds of spinach were sowed at the end of November. An aqueous solution of Compound No. 2 (100 ppm) was sprayed to plants 88 days thereafter. The height of the plants and the length of the stems, respectively, were measured 17 days after spraying. The results are set forth in the following table.

| Compound No. | Conc. (ppm) | Height (cm) | Stem length (cm) |
|---|---|---|---|
| 2 | 100 | 23.3 | 20.0 |
| Control | — | 35.5 | 40.2 |

TEST 15

An aqueous solution of the compound mentioned below with a specified concentration was sprayed onto one of branches 1 m in length of an apple tree at the end of May. The items mentioned in the following table were observed.

| Compound No. | Conc. (ppm) | A(%) | B(%) |
|---|---|---|---|
|  | 1000 | 105.9 | 250.7 |
| 2 | 500 | 104.9 | 254.1 |
|  | 100 | 105.4 | 272.9 |
|  | 1000 | 109.7 | 260.8 |
| 13 | 500 | 146.6 | 269.0 |
|  | 100 | 114.9 | 273.8 |
| Control | — | 161.0 | 264.3 |

Note:
1) "A" in the table refers to "the elongation ratio (%) of current year shoot" which is calculated according to the following formula.

The length of the current year shoot at the time of the elongation stopping $$A\ (\%) = \frac{\text{The length of the current year shoot at the time of spray of the test solution}} \times 100$$

In this test, the measurement was conducted 99 days after the spray of the test solution.

2) "B" in the table refers to "growth ratio of fruit" which is calculated according to the following formula.

$$B\ (\%) = \frac{\text{Diameter of fruit 113 days after spray}}{\text{Diameter of fruit at the time of the spray of the test solution}} \times 100$$

TEST 16

An aqueous solution (500 ppm) of the compound No. 2 was sprayed onto 5 branches of a grape bearing female buds at the 20th day before the full bloom thereof. The elongation ratio (%) of the current year shoot compared with the length of the current year shoot at the time of spraying was measured at the 50th day after spraying, and the fruits harvested during 120 days after spraying was weighed.

| Compound No. | Elongation ratio of the current year shoot (%) | Fruits weight (g) |
|---|---|---|
| 2 | 392.9 | 387.0 |
| Control | 611.4 | 232.4 |

TEST 17

An aqueous solution (200 ppm) of the compound No. 2 was sprayed onto branches of a mandarin tree bearing fruits at the end of December. The state of overgrowth of pericarp of mandarins was measured at the 25th day after spraying. The results are set forth in the following table.

| Compound No. | State of Pericarp in Mandarin (%) | | | | A |
|---|---|---|---|---|---|
| | Non | Slight | Medium | Remarkable | |
| 2 | 84.3 | 14.9 | 0.8 | 0 | 5.5 |
| Control | 48.4 | 46.2 | 5.0 | 0 | 18.7 |

In the above table, A refers to a index of pericarp of mandarin which is calculated according to the following formula:

$$A = \frac{(\text{No. of non}) + (\text{No. of medium} \times 2) + (\text{No. of remarkable} \times 3)}{\text{Total fruit number} \times 3} \times 100$$

TEST 18

Seedlings of potmum grown in a seed bed were transplanted to two flower pots at the beginning of May. Lateral buds were pinched at the 7th day after transplantation. An aqueous solution of the test compound mentioned below with a specified concentration was sprayed onto the plants. The height of plants (the elongation after pinching) and the flower diameter were measured 55 days after spray. The relative values compared with the non-treated plants were also calculated.

| Compound No. | Conc. (ppm) | Height | | Flower diameter | |
|---|---|---|---|---|---|
| | | cm | % | cm | % |
| 2 | 250 | 22.5 | 89.2 | 10.3 | 108.4 |
| | 125 | 20.9 | 83.6 | 9.9 | 10.42 |
| | 63 | 24.1 | 96.0 | 10.2 | 107.4 |
| 13 | 250 | 20.8 | 83.2 | 9.0 | 94.7 |
| | 125 | 19.9 | 79.7 | 9.4 | 98.9 |
| | 63 | 22.0 | 88.0 | 8.9 | 93.7 |
| 15 | 250 | 19.4 | 77.6 | — | — |
| | 125 | 21.2 | 84.8 | 8.5 | 89.3 |
| | 63 | 20.4 | 81.6 | 10.3 | 108.4 |

Practical and presently-preferred embodiments for the preparation of the compound (II) are illustratively shown in the following examples.

1. Preparation of [3-methyl-5-(2,6,6-trimethyl-1-cyclohexenyl)-2(trans),4(trans)-pentadienyl]dimethylamine A solution of 3-methyl-5-(2,6,6-trimethyl-1-cyclohexenyl)-2(trans)4(trans)-pentadienoic acid (4.5 g) in absolute benzene (60 cc) was added to thionylchloride (5.8 g) under cooling and the mixture was allowed to stand for 2 hours at room temperature. The excess thionylchloride was distilled off under reduced pressure, and the residue was dissolved in absolute benzene (30 cc). The mixture was added dropwise to a mixture of dimethylamine (20 cc) and absolute benzene (10 cc) under cooling, and the mixture was allowed to stand for 2 hours. The reaction mixture was washed with water and dried over magnesium sulfate. The solvent was distilled off, and the oily residue was distilled at 138°–143° C under reduced pressure (0.3 mmHg) to give an oil (2.6 g) of N,N-dimethyl-3-methyl-5-(2,6,6-trimethyl-1-cyclohexenyl)-3(trans),4(trans)-pentadienoic acid amide. To a solution of lithium aluminum hydride (0.5 g) in dry ether (25 cc) was added dropwise a solution of N,N-dimethyl-3-methyl-5-(2,6,6-trimethyl-1-cyclohexenyl)-2(trans),4(trans)-pentadienoic acid amide (2.5 g) in dry ether (25 cc) under cooling, and the reaction mixture was refluxed for 2 hours. Thereto was added water in order to decompose the excess lithium aluminum hydride, and the reaction mixture was filtered. The filtrate was extracted with ether and the ether layer was dried. The solvent was distilled off, and the residue was distilled at 118°–124° C under reduced pressure (0.8 mmHg) to give an oil (1.3 g) of [3-methyl-5-(2,6,6-trimethyl-1-cyclohexenyl)-2(trans),4(trans)-pentadienyl]-dimethylamine.

2. Preparation of [3-(2,6,6-trimethyl-1-cyclohexenyl)-2(trans)-propenyl]dimethylamine To a solution of 3-(2,6,6-trimethyl-1-cyclohexenyl)-2(trans)-acrylic acid (5.0 g) in dry benzene (15 cc) was added thionylchloride (10 cc) at room temperature, and the mixture was allowed to stand overnight. The excess thionylchloride was distilled off under reduced pressure, and the residue was dissolved in dry ether (20 cc), and the ethereal solution was added dropwise to a solution of dimethylamine (5.0 g) in ether (20 cc) under cooling at 0° C during 10 minutes. The mixture was stirred for 2 hours, washed with water and dried. The solvent was distilled off under reduced pressure to give a yellowish oil (5.7 g) of N,N-dimethyl-3-(2,6,6-trimethyl-1-cyclohexenyl)-2(trans)-acrylic acid amide as the residue. A solution of this oil in ether (10 cc) was added dropwise to a suspension of lithium aluminum hydride (2.0 g) in dry ether (50 cc) under cooling at 0°–5° C, and the mixture was refluxed for 5 hours. Thereto was added dropwise a saturated aqueous solution of ammonium chloride (15 cc), and the mixture was stirred for 15 minutes and filtered. The filtrate was extracted with hydrochloric acid and the extract was washed with ether. The aqueous solution was adjusted to an alkalinity by adding an aqueous solution of sodium hydroxide and extracted with ether. The ether layer was washed with an aqueous solution of sodium chloride and dried. The solvent was distilled off under reduced pressure. The residue was distilled at 98°–99° C under reduced pressure (5 mmHg) to give a colorless oil (4.0 g) of [3-(2,6,6-trimethyl-1-cyclohexenyl)-2(trans)-propenyl]dimethylamine.

3. Preparation of 4-[1-methyl-3-(2,6,6-trimethyl-2-cyclohexenyl)-2(trans)-propenyl]morpholine A solution of 1-methyl-3-(2,6,6-trimethyl-2-cyclohexenyl)-2(trans)-propenol in a mixed solvent of dry ether (200 cc) and pyridine (4 cc) was added dropwise to a solution of phosphorus tribromide (29.6 g) in dry ether (85 cc) under cooling at below 10° C. The mixture was stirred for 5 hours at 5°–10° C and allowed to stand over night. The mixture was poured into ice-water, and the organic layer was washed with water and dried. The organic layer was added dropwise to a solution of morpholine (26.7 g) in dry ether (80 cc) under cooling, and the reaction mixture was stirred for 5 hours under cooling at 5°–10° C. The mixture was washed with water and extracted with hydrochloric acid. The extract was adjusted to an alkalinity by adding an aqueous solution of sodium bicarbonate and extracted with ether. The ether layer was washed with water and dried. The solvent was distilled off under reduced pressure, and the residue was distilled under reduced pressure (1 mmHg) at 128°–130° C to give an oil (8.2 g) of 4-[1-methyl-3-(2,6,6-trimethyl-2-cyclohexenyl)-2(trans)propenyl]morpholine.

4. Preparation of 1-[1-methyl-3-(2,6,6-trimethyl-2-cyclohexenyl)-2(trans)-propenyl]piperidine With a mixture of 1-methyl-3-(2,6,6-trimethyl-2-cyclohexenyl)-2(trans)-propenol (10.0 g), phosphorus bromide (7.4 g) and piperidine (6.6 g), an oil (3.0 g) of 1-[1-methyl-3-(2,6,6-trimethyl-2-cyclohexenyl)-2(trans)-propenyl]piperidine, b.p. 143°–149° C (1 mmHg), was obtained according to a similar manner to the preceding preparation 3.

5. Preparation of [1-methyl-3-(2,6,6-trimethyl-2-cyclohexenyl)-2(trans)-propenyl]dimethylamine A solution of 1-methyl-3-(2,6,6-trimethyl-2-cyclohexenyl)-2(trans)-propenol (30.0 g) and piperidine (2.6 cc) in absolute ether (140 cc) was added dropwise to a solution of phosphorus tribromide (20.0 g) in absolute ether (100 cc) under cooling at 5°–10° C. The reaction mixture was stirred for several hours and allowed to stand over night. Thereto was added water, and the aqueous solution was extracted with ether. The ether layer was washed with an aqueous solution of sodium bicarbonate and dried over magnesium sulfate. The solvent was distilled off, and the residue was dissolved in ether (100 cc). Thereto was added dropwise a solution of dimethylamine (12.4 g) in ether (50 cc) during 4 hours under cooling, and the reaction mixture was stirred for 24 hours at room temperature. The reaction mixture was poured into ice, and the mixture was acidified by adding hydrochloric acid. The aqueous layer was alkalized by adding an aqueous solution of sodium hydroxide, and then the mixture was extracted with ether. The ether layer was washed with water and dried over magnesium sulfate. The solvent was distilled off under reduced pressure and the oily residue was distilled at 95°–96° C under reduced pressure (3 mmHg) to give an oil of [1-methyl-3-(2,6,6-trimethyl-2-cyclohexanyl)-2(trans)-propenyl]dimethylamine.

Analysis: $C_{15}H_{27}N$; Calculated: C 81.37, H 12.30, N 6.32; Found: C 81.20, H 12.17, N 6.54.

6. Preparation of a mixture consisting of 1-[1-methyl-3-(2,6,6-trimethyl-2-cyclohexenyl)-2-propenyl]pyrrolidine and 1-[1-methyl-3-(2,6,6-trimethyl-1-cyclohexenyl)-2-propenyl]pyrrolidine A mixture of 4-(2,6,6-trimethyl-2-cyclohexenyl)-3-butene-2-one (19.2 g), formylpyrrolidine (30.0 g) and formic acid (15.0 g) was sealed and heated at 190° C for 6 hours. After the completion of the reaction, the reaction mixture was acidified by adding 10% hydrochloric acid and was washed with ether. The reaction mixture was alkalized by adding diluted aqueous solution of sodium hydroxide, and then extracted with ether. The ether layer was dried and the solvent was distilled off. The oily residue was distilled at 161°–163° C under reduced pressure (12–13 mmHg) to give an oily mixture (6.0 g) consisting of 1-[1-methyl-3-(2,6,6-trimethyl-1-cyclohexenyl)-2-propyenl] pyrrolidine and 1-[1-methyl-3-(2,6,6-trimethyl-2-cyclohexenyl)-2-propenyl]-pyrrolidine.

It was observed in the I.R. spectrum of this oil that the absorption at 1665 cm$^{-1}$ based on the carbonyl group, which was existing in the form of 4-(2,6,6-trimethyl-2-cyclohexenyl)-3-butene-2-one, has disappeared.

Analysis: $C_{17}H_{29}N$; Calculated: C 82.52, H 11.18, N 5.66; Found: C 82.38, H 11.61, N 5.64.

7. Preparation of a mixture consisting of [1-methyl-3-(2,6,6-trimethyl-1-cyclohexenyl)-2-propenyl]dimethylamine and [1-methyl-3-(2,6,6-trimethyl-2-cyclohexenyl)-2-propenyl]dimethylamine A mixture of 4-(2,6,6-trimethyl-1-cyclohexenyl)-3-butene-2-one (33.4 g), dimethylformamide (43.8 g) and formic acid (27.6 g) was sealed and heated at 190° C for 14 hours. After the completion of the reaction, the reaction mixture was dissolved in diluted hydrochloric acid and the aqueous solution was washed with ether. The aqueous solution was alkalized by adding diluted aqueous solution of sodium hydroxide and extracted with ether. The ether layer was washed with water, dried and the solvent was distilled off under reduced pressure. The oily residue was distilled under reduced pressure (33 mmHg) at 103°–104° C to give an oily mixture consisting of [1-methyl-3-(2,6,6-trimethyl-1-cyclohexenyl)-2-propenyl]dimethylamine and [1-methyl-3-(2,6,6-trimethyl-2-cyclohexenyl)-2-propenyl]dimethylamine (1:1).

It was observed in the I.R. spectrum of this oil that the absorption at 1665 cm$^{-1}$ based on the carbonyl group, which was existing in that of 4-(2,6,6-trimethyl-2-cyclohexenyl)-3-butene-2-one, has disappeared.

Analysis: $C_{15}H_{27}N$; Calculated: C 81.75, H 11.89, N 6.35; Found: C 81.87, H 12.23, N 6.49.

Practical and presently-preferred embodiments for the preparation of the present invention are illustratively shown in the following non-limitative examples

EXAMPLE 1 a. To a solution of [1-methyl-3-(2,6,6-trimethylcyclohexyl)propyl]dimethylamine (3.0 g) in benzene (20 cc) was added methyliodide (10.0 g), and the mixture was allowed to stand over night. Precipitated crystals were gathered by filtration, and recrystallized from a mixed solvent of benzene and ether to give colorless crystals (4.4 g) of [1-methyl-3-(2,6,6-trimethylcyclohexyl)propyl]trimethylammonium iodide.

N.M.R. spectrum:
| | | |
|---|---|---|
| $\tau = 9.00 - 9.23$ | | 9H |
| $\tau = 8.50$ | (doublet) | 3H |
| $\tau = 6.58$ | (singlet) | 9H | b. A mixture of [1-methyl-3-(2,6,6-trimethylcyclohexyl)propyl]trimethylammonium iodide (5.0 g), silver bromide (5.0 g) and absolute methanol (10 cc) was refluxed for 3 hours, and the reaction mixture was filtered. The filtrate was concentrated and the concentrate was recrystallized from a mixed solvent of benzene and ether to give colorless crystals (3.6 g) of [1-methyl-3-(2,6,6-trimethylcyclohexyl)propyl]trimethylammonium bromide.

N.M.R. spectrum:
| | | |
|---|---|---|
| $\tau = 9.00 - 9.23$ | | 9H |
| $\tau = 8.50$ | (doublet) | 3H |
| $\tau = 6.60$ | (singlet) | 9H | c. A mixture of [1-methyl-3-(2,6,6-trimethylcyclohexyl)propyl]trimethylammonium iodide (5.0 g) and silver chloride (6.0 g) was treated according to a similar manner to the Example 1 (b), and colorless crystals (2.3 g) of [1-methyl-3-(2,6,6-trimethylcyclohexyl)propyl]trimethylammonium chloride were obtained.

N.M.R. spectrum:
| | | |
|---|---|---|
| $\tau = 9.00 - 9.21$ | | 9H |
| $\tau = 8.48$ | (doublet) | 3H |
| $\tau = 6.57$ | (singlet) | 9H |

EXAMPLE 2

To a solution of [1-methyl-3-(2,6,6-trimethyl-1-cyclohexenyl)propyl]dimethylamine (2.0 g) in dry ether (20 cc) was added methyliodide (2.0 g), and the mixture was allowed to stand overnight. Precipitated crystals were gathered by filtration and recrystallized from a mixed solvent of ethanol, benzene and ether to give colorless crystals (3.0 g) of [1-methyl-3-(2,6,6-trimethyl-1-cyclohexenyl)propyl]trimethylammonium iodide, m.p. 220°–222° C.

Analysis: $C_{16}H_{32}NJ$; Calculated: C 52.60, H 8.83, N 3.83; Found: C 52.45, H 8.51, N 3.95.

N.M.R. spectrum:
| | | |
|---|---|---|
| $\tau = 9.00$ | (singlet) | 6H |
| $\tau = 8.44$ | (doublet) | 3H |
| $\tau = 8.33$ | (singlet) | 3H |
| $\tau = 6.60$ | (singlet) | 9H |
| $\tau = 6.10$ | (multiplet) | 1H |

EXAMPLE 3 a. Crystals (4.5 g) of [1-methyl-3-(2,6,6-trimethyl-2-cyclohexenyl)-2(trans)-propenyl]trimethylammonium iodide, m.p. 155° C, were obtained by treating [1-methyl-3-(2,6,6-trimethyl-2-cyclohexenyl)-2(trans)-propenyl]dimethylamine (3.0 g) similarly to the Example 1 (a).

Analysis: $C_{16}H_{30}NJ$; Calculated: C 52.89, H 8.32, N 3.85, J 35.57; Found: C 52.86, H 8.50, N 3.83, J 35.48.

N.M.R. spectrum:
| | | |
|---|---|---|
| $\tau = 9.16$ | (doublet) | 3H |
| $\tau = 9.10$ | (singlet) | 3H |
| $\tau = 8.44$ | (multiplet) | 6H |
| $\tau = 6.63$ | (singlet) | 9H |
| $\tau = 5.40$ | (multiplet) | 1H |
| $\tau = 3.7 - 4.72$ | (multiplet) | 3H | b. A solution of [1-methyl-3-(2,6,6-trimethyl-2-cyclohexenyl)-2(trans)-propenyl]trimethylammonium iodide (2.0 g) and silver bromide (3.0 g) in absolute methanol (10 cc) was treated according to a similar manner to the Example 1 (b), and the concentrate thus obtained was recrystallized from a mixed solvent of ethanol and ether to give colorless crystals (1.2 g) of [1-methyl-3-(2,6,6-trimethyl-2-cyclohexenyl)-2(trans)-propenyl]trimethylammonium bromide, m.p. 258°–260° C.

Analysis: $C_{16}H_{30}NBr$; Calculated: Br 25.26; Found: Br 25.21.

N.M.R. spectrum:
| | | |
|---|---|---|
| $\tau = 9.15$ | (singlet) | 3H |
| $\tau = 9.08$ | (singlet) | 3H |
| $\tau = 8.44$ | (multiplet) | 6H |
| $\tau = 6.60$ | (singlet) | 9H |
| $\tau = 5.40$ | (multiplet) | 1H |
| $\tau = 3.80 - 4.80$ | | 3H | c. A solution of [1-methyl-3-(2,6,6-trimethyl-2-cyclohexenyl)-2(trans)-propenyl]trimethylammonium iodide (2.0 g) and silver chloride (3.0 g) in absolute methanol (10 cc) was treated according to a similar manner to the Example 1 (b), and the concentrate thus obtained was recrystallized from a mixed solvent of ethanol and ether to give colorless crystals (1.0 g) of [1-methyl-3-(2,6,6-trimethyl-2-cyclohexenyl)-2(trans)-propenyl]trimethylammonium chloride.

Analysis: $C_{16}H_{30}NCl$; Calculated: C 70.69, H 11.12, N 5.15, Cl 13.04; Found: C 70.45, H 11.30, N 5.39, Cl 12.82.

N.M.R. spectrum:
| | | |
|---|---|---|
| $\tau = 9.20$ | (singlet) | 3H |
| $\tau = 9.10$ | (singlet) | 3H |
| $\tau = 8.44$ | (multiplet) | 6H |
| $\tau = 6.60$ | (singlet) | 9H |
| $\tau = 5.40$ | (multiplet) | 1H |

| $\tau = 3.80 - 4.80$ | (multiplet) | 3H |

| $\tau = 5.43$ | (multiplet) | 1H |
| $\tau = 3.75 - 4.72$ | | 3H |

EXAMPLE 4

With a solution of [1-methyl-3-(2,6,6-trimethyl-2-cyclohexenyl)-2(trans)-propenyl]dimethylamine (5.4 g) and ethyliodide (15.0 g) in benzene (20 cc), colorless crystals (5.6 g) of [1-methyl-3-(2,6,6-trimethyl-2-cyclohexenyl)-2(trans)-propenyl]dimethylethylammonium iodide, m.p. 133° C, were obtained according to a similar manner to the Example 1 (a).

Analysis: $C_{17}H_{32}NJ$; Calculated: C 54.11, H 8.55, N 3.71, J 33.63; Found: C 54.19, H 8.40, N 3.54, J 33.61.

| N.M.R. spectrum: | | |
|---|---|---|
| $\tau = 9.15$ | (doublet) | 3H |
| $\tau = 9.07$ | (singlet) | 3H |
| $\tau = 8.29 - 8.85$ | | 9H |
| $\tau = 6.76$ | (singlet) | 6H |
| $\tau = 6.32$ | (quartet) | 2H |
| $\tau = 5.40$ | (multiplet) | 1H |
| $\tau = 3.83 - 4.64$ | | 3H |

EXAMPLE 5

A mixture of [1-methyl-3-(2,6,6-trimethyl-2-cyclohexenyl)-2(trans)-propenyl]dimethylamine (2.3 g) and ethylbromide (6.0 g) was refluxed for 3 hours, and then the excess ethylbromide was distilled off. The residue was recrystallized from a mixed solvent of benzene and ether to give colorless crystals (0.9 g) of [1-methyl-3-(2,6,6-trimethyl-2-cyclohexenyl)-2(trans)-propenyl]dimethylethylammonium bromide.

Analysis: $C_{17}H_{32}NBr$; Calculated: C 61.81, H 9.76, N 4.24, Br 24.19; Found: C 61.17, H 9.64, N 4.09, Br 24.02.

| N.M.R. spectrum: | | |
|---|---|---|
| $\tau = 9.17$ | (doublet) | 3H |
| $\tau = 9.09$ | (singlet) | 3H |
| $\tau = 8.30 - 8.85$ | | 9H |
| $\tau = 6.77$ | (singlet) | 6H |
| $\tau = 6.32$ | (quartet) | 2H |
| $\tau = 5.50$ | (multiplet) | 1H |
| $\tau = 3.77 - 4.78$ | | 3H |

EXAMPLE 6

A solution of [1-methyl-3-(2,6,6-trimethyl-2-cyclohexenyl)-2(trans)-propenyl]dimethylamine (5.0 g) and 1-propylbromide (6.0 g) in absolute methanol (10 cc) was refluxed for 3 hours, and the solvent of the reaction mixture was distilled off under reduced pressure. To the residue were added benzene and ether, and precipitated crystals were gathered by filtration to give colorless crystals (0.8 g) of [1-methyl-3-(2,6,6-trimethyl-2-cyclohexenyl)-2(trans)-propenyl]dimethylpropylammonium bromide.

| N.M.R. spectrum: | | |
|---|---|---|
| $\tau = 9.18$ | (doublet) | 3H |
| $\tau = 9.10$ | (singlet) | 3H |
| $\tau = 8.97$ | (triplet) | 3H |
| $\tau = 8.28 - 8.77$ | | 8H |
| $\tau = 6.73$ | (doublet) | 6H |
| $\tau = 6.23 - 6.65$ | | 2H |

EXAMPLE 7 a. A solution of [1-methyl-3-(2,6,6-trimethyl-2-cyclohexenyl)-2(trans)-propenyl]dimethylamine (5.0 g) and 1-propylbromide (6.0 g) in absolute methanol (10 cc) was refluxed for 3 hours, and the solvent of the reaction mixture was distilled off under reduced pressure. To the residue was added a solution of potassium iodide (5.7 g) in a mixed solvent of water and a small amount of ethanol, and the mixture was allowed to stand for 30 minutes. The mixture was concentrated to dryness under reduced pressure, and the residue was dissolved in chloroform. After the filtration of the chloroform layer, the solvent of the filtrate was distilled off, and the residue was recrystallized from a mixed solvent of benzene and ether to give colorless crystals (6.05 g) of [1-methyl-3-(2,6,6-trimethyl-2-cyclohexenyl)-2(trans)-propenyl]dimethylpropylammonium iodide.

| N.M.R. spectrum: | | |
|---|---|---|
| $\tau = 9.15$ | (doublet) | 3H |
| $\tau = 9.10$ | (singlet) | 3H |
| $\tau = 8.97$ | (triplet) | 3H |
| $\tau = 8.28 - 8.78$ | | 8H |
| $\tau = 6.75$ | (singlet) | 6H |
| $\tau = 6.30 - 6.67$ | | 2H |
| $\tau = 5.43$ | (multiplet) | 1H |
| $\tau = 3.70 - 4.70$ | | 3H | b. With a solution of [1-methyl-3-(2,6,6-trimethyl-2-cyclohexenyl)-2(trans)-propenyl]dimethylpropylammonium iodide (1.0 g) and silver chloride (1.0 g) in absolute methanol (10 cc), colorless crystals (0.4 g) of [1-methyl-3-(2,6,6-trimethyl-2-cyclohexenyl)-2(trans)-propenyl]dimethylpropylammonium chloride were obtained according to a similar manner to the Example 1 (b).

| N.M.R. spectrum: | | |
|---|---|---|
| $\tau = 9.18$ | (doublet) | 3H |
| $\tau = 9.11$ | (singlet) | 3H |
| $\tau = 8.98$ | (triplet) | 3H |
| $\tau = 8.29 - 8.80$ | | 8H |
| $\tau = 6.73$ | (doublet) | 6H |
| $\tau = 6.27 - 6.65$ | | 2H |
| $\tau = 5.12 - 5.81$ | | 1H |
| $\tau = 3.78 - 4.73$ | | 3H |

EXAMPLE 8

A solution of [1-methyl-3-(2,6,6-trimethyl-2-cyclohexenyl)-2(trans)-propenyl]dimethylamine (3.0 g) and 1-heptylbromide (3.0 g) in methanol (30 cc) was refluxed for 3 hours, and thereto was added water (100 cc). The mixture was washed with ether, and thereto was added potassium iodide (10.0 g). The reaction mixture was allowed to stand for 30 minutes, and then extracted with chloroform. The chloroform layer was washed with a saturated aqueous solution of sodium thiosulfate and dried over sodium sulfate. The solvent was distilled off to give an oil (4.8 g) of [1-methyl-3-(2,6,6-trimethyl-2-cyclohexenyl)-2(trans)-propenyl]dimethylheptylammonium iodide.

It was observed in the I.R. spectrum of this oil that the absorptions at 2750 and 2800 cm-1 based on the tertiary amine, which were existing in that of [1-methyl-3-(2,6,6-trimethyl-2-cyclohexenyl)-2(trans)-propenyl]dimethylamine, have disappeared.

U.V. spectrum: (EtOH), $\lambda_{max} = 210$ m$\mu$

EXAMPLE 9

A solution of [1-methyl-3-(2,6,6-trimethyl-2-cyclohexenyl)-2(trans)-propenyl]dimethylamine (3.0 g) and 1-octylbromide (3.0 g) in methanol (50 cc) was refluxed for 3 hours, and water was added thereto. The mixture was washed with ether and thereto was added potassium iodide (10.0 g). The reaction mixture was treated according to a similar manner to the Example 8 to give an oil (5.0 g) of [1-methyl-3-(2,6,6-trimethyl-2-cyclohexenyl)-2(trans)-propenyl]dimethyloctylammonium iodide.

It was observed in the I.R. spectrum of this oil that the absorptions at 2750 and 2800 cm-1 based on the tertiary amine, which were existing in that of [1-methyl-3-(2,6,6-trimethyl-2-cyclohexenyl)-2(trans)-propenyl]dimethylamine, have disappeared.

U.V. spectrum: (EtOH) $\lambda_{max} = 210$ m$\mu$

EXAMPLE 10

To a solution of [3-methyl-5-(2,6,6-trimethyl-1-cyclohexenyl)-2-(trans),4(trans)-pentadienyl]dimethylamine (1.3 g) in small amount of absolute ethanol were added methyliodide (2.0 g) and ether (50 cc) under cooling, and the reaction mixture was allowed to stand. Precipitated crystals were gathered by filtration and recrystallized from a mixed solvent of benzene and chloroform to give crystals (0.6 g) of [3-methyl-5-(2,6,6-trimethyl-1-cyclohexenyl)-2(trans),4(trans)-pentadienyl]trimethylammonium iodide, m.p. 174°–176° C.

Analysis: $C_{18}H_{32}NJ$; Calculated: J 32.59; Found: J 31.96.

EXAMPLE 11

A solution of [1-methyl-3-(2,6,6-trimethyl-2-cyclohexenyl)-2(trans)-propenyl]dimethylamine (2.7 g) and 1,2-ethyldibromide (2.0 g) in ethanol (30 cc) was refluxed for 3 hours, and the solvent of the reaction mixture was distilled off under reduced pressure. To the residue was added water (100 cc), and the aqueous solution was washed with ether, and then thereto was added potassium iodide (10.0 g). The reaction mixture was allowed to stand for 30 minutes, and extracted with chloroform. The chloroform layer was dried and the chloroform was distilled off. The residue was recrystallized from ethanol to give colorless crystals (1.8 g) of [1-methyl-3-(2,6,6-trimethyl-2-cyclohexenyl)-2(trans)-propenyl]dimethyl-(2-bromoethyl)ammonium iodide.

It was observed in the I.R. spectrum of this oil that the absorptions at 2750 and 2800 cm-1 based on the tertiary amine, which were existing in that of [1-methyl-3-(2,6,6-trimethyl-2-cyclohexenyl)-2(trans)-propenyl]dimethylamine, have disappeared.

EXAMPLE 12

With a solution of [1-methyl-3-(2,6,6-trimethyl-2-cyclohexenyl)-2(trans)-propenyl]dimethylamine (2.3 g), 1,3-propyldibromide (2.0 g) and potassium iodide (10.0 g) in ethanol (50 cc), a yellowish oil (3.2 g) of [1-methyl-3-(2,6,6-trimethyl-2-cyclohexenyl)-2(trans)-propenyl]dimethyl(3-bromopropyl)ammonium iodide was obtained according to a similar manner to the Example 11.

It was observed in the I.R. spectrum of this oil that the absorptions at 2750 and 2800 cm-1 based on the tertiary amine, which were existing in that of [1-methyl-3-(2,6,6-trimethyl-2-cyclohexenyl)-2(trans)-propenyl]dimethylamine, have disappeared.

EXAMPLE 13

With a solution of [1-methyl-3-(2,6,6-trimethyl-2-cyclohexenyl)-2(trans)-propenyl]dimethylamine (2.0 g), 3-propargylbromide (1.1 g) and potassium iodide (10.0 g) in methanol (30 cc), a yellowish oil (3.2 g) of [1-methyl-3-(2,6,6-trimethyl-2-cyclohexenyl)-2(trans)-propenyl]dimethylpropargylammonium iodide was obtained according to a similar manner to the Example 8.

I.R. spectrum: 2140 cm-1

It was observed in the I.R. spectrum of this oil that the absorptions at 2750 and 2800 cm-1 based on the tertiary amine, which were existing in that of [1-methyl-3-(2,6,6-trimethyl-2-cyclohexenyl)-2(trans)-propenyl]dimethylamine, have disappeared.

EXAMPLE 14

A solution of [1-methyl-3-(2,6,6-trimethylcyclohexyl) propyl]dimethylamine (1.6 g) and $\alpha$,3,4-trichlorotoluene (1.6 g) in absolute methanol (10 cc) was refluxed for 3 hours, and the solvent of the reaction mixture was distilled off. The residue was dissolved in a mixed solvent of water (100 cc) and a small amount of ethanol, and potassium iodide (4.0 g) was added thereto. Thirty minutes thereafter, the reaction mixture was concentrated to dryness under reduced pressure, and the residue was dissolved in chloroform. After the filtration of the chloroform layer, the solvent of the filtrate was distilled off, and the residue was recrystallized from a mixed solvent of benzene and ether to give colorless crystals (2.7 g) of [1-methyl-3-(2,6,6-trimethylcyclohexyl)-propyl]dimethyl(3,4-dichlorobenzyl)ammonium iodide, m.p. 193°–195° C.

Analysis: $C_{22}H_{36}NCl_2J$; Calculated: C 51.57, H 7.08, N 2.73, Cl 13.84, J 24.77; Found: C 51.84, H 6.95, N 2.85, Cl 13.62, J 24.69.

EXAMPLE 15

A solution of [3-(2,6,6-trimethyl-1-cyclohexenyl)-2(trans)-propenyl]dimethylamine (2.0 g) in dry ether (20 cc) was added to methyliodide (2.0 g), and the reaction mixture was allowed to stand over night. Precipitated crystals were gathered by filtration, and recrystallized from a mixed solvent of ethanol, benzene and ether to give colorless crystals (2.3 g) of [3-(2,6,6-trimethyl-1-cyclohexenyl)-2(trans)-propenyl]trimethylammonium iodide, m.p. 180° C.

EXAMPLE 16

With a solution of [1-methyl-3-(2,6,6-trimethylcyclohexyl)propyl]dimethylamine (1.6 g), $\alpha$,2,4-trichlorotoluene (1.6 g) and potassium iodide (4.0 g) in absolute methanol (10 cc), colorless crystals (2.4 g) of [1-methyl-3-(2,6,6-trimethyl cyclohexyl)propyl]dimethyl(2,4-dichlorobenzyl)ammonium iodide were obtained according to a similar manner to the Example 14.

| N.M.R. spectrum: | | | |
|---|---|---|---|
| | τ = 8.96 – 9.27 | | 9H |
| | τ = 8.38 | (doublet) | 3H |
| | τ = 6.86 | (singlet) | 3H |
| | τ = 6.81 | (singlet) | 3H |
| | τ = 5.84 | (multiplet) | 1H |
| | τ = 5.06 | (singlet) | 2H |
| τ = 2.58 | τ = 2.58 | (doublet) | 1H |
| | τ = 1.80 | (doublet) | 1H |
| | τ = 2.51 | (doublet) | 1H |

EXAMPLE 17 a. A solution of [1-methyl-3-(2,6,6-trimethyl-2-cyclohexenyl)-2(trans)-propenyl]dimethylamine (3.0 g) and α,3,4-trichlorotoluene (4.0 g) in methanol (15 cc) was refluxed for 2 hours, and thereto were added ethanol (40 cc) and then an aqueous solution of potassium iodide (3.0 g). The solvent of the reaction mixture was distilled off under reduced pressure, and the residue was recrystallized from a mixed solvent of methanol and ether to give colorless crystals (4.0 g) of [1-methyl-3-(2,6,6-trimethyl-2-cyclohexenyl)-2(trans)-propenyl]dimethyl(3,4-dichlorobenzyl)ammonium iodide, m.p. 160°–165° C.

Analysis: $C_{22}H_{32}NCl_2J$; Calculated: C 51.98, H 6.35, N 2.76, J 24.97; Found: C 51.70, H 6.35, N 2.76, J 25.19.

b. A mixture of [1-methyl-3-(2,6,6-trimethyl-2-cyclohexenyl)-2(trans)-propenyl]dimethyl(3,4-dichlorobenzyl)ammonium iodide (1.5 g), silver bromide (3.5 g) and sodium hydroxide (10 cc) was refluxed for 4 hours, and after the filtration of the reaction mixture, the solvent of the filtrate was distilled off. The residue was added to a mixed solvent of ether, methanol and benzene, and precipitated crystals were gathered by filtration to give humid colorless crystals (1.0 g) of [1-methyl-3-(2,6,6-trimethyl-2-cyclohexenyl)-2(trans)-propenyl]dimethyl-(3,4-dichlorobenzyl)ammonium bromide.

Analysis: $C_{22}H_{32}NCl_2Br$; Calculated: C 57.28, H 6.99, N 3.04, Br 17.32; Found: C 57.18, H 7.00, N 3.26, Br 17.54.

EXAMPLE 18

A solution of [1-methyl-3-(2,6,6-trimethyl-2-cyclohexenyl)-2(trans)-propenyl]dimethylamine (2.0 g) and α,3,4-trichlorotoluene (3.0 g) in methanol (10 cc) was refluxed for 2 hours, and the solvent of the reaction mixture was distilled off under reduced pressure. The residue was recrystallized from a mixed solvent of benzene and ether to give hygroscopic, colorless crystals (2.1 g) of [1-methyl-3-(2,6,6-trimethyl-2-cyclohexenyl)-2(trans)-propenyl]dimethyl(3,4-dichlorobenzyl)ammonium chloride.

Analysis: $C_{22}H_{32}NCl_3$; Calculated: C 63.39, H 7.74, N 3.36, Cl 25.51; Found: C 63.47, H 7.94, N 3.04, Cl 25.81.

EXAMPLE 19

A mixture of [1-methyl-3-(2,6,6-trimethyl-2-cyclohexenyl)-2(trans)-propenyl]dimethylamine (2.0 g), α,2,4-trichlorotoluene (3.0 g) and methanol (10 cc) was refluxed for 5 hours, and the solvent of the reaction mixture was distilled off under reduced pressure. The residue was dissolved in a small amount of benzene and thereto was added a large amount of ether. The precipitated oil was gathered by decantation and dissolved in a small amount of benzene and thereto was further added a large amount of ether. The solvent was distilled off to give colorless oil (4.5 g) of [1-methyl-3-(2,6,6-trimethyl-2-cyclohexenyl)-2(trans)-propenyl]dimethyl(2,4-dichlorobenzyl)ammonium chloride.

It was observed in the I.R. spectrum of this oil that the absorptions at 2750 and 2800 cm-1 based on the tertiary amine, which were existing in that of the starting material, have disappeared.

EXAMPLE 20 a. A mixture of [1-methyl-3-(2,6,6-trimethyl-2-cyclohexenyl)-2(trans)-propenyl]dimethylamine (3.0 g), α,2,4-trichlorotoluene (3.0 g) and absolute methanol (10 cc) was refluxed for 6 hours, and the solvent of the reaction mixture was distilled off under reduced pressure. The residue was dissolved in ethanol (20 cc) and a solution of potassium iodide (3.0 g) in water (5 cc) was added thereto. The reaction mixture was concentrated to dryness, and the residue was dissolved in chloroform. After the filtration of the chloroform layer, the solvent of the filtrate was distilled off under reduced pressure. The residue was recrystallized twice from a mixed solvent of methanol and ether to give colorless crystals (5.2 g) of [1-methyl-3-(2,6,6-trimethyl-2-cyclohexenyl)-2(trans)-propenyl]dimethyl(2,4-dichlorobenzyl)ammonium iodide mono-hydrate.

Analysis: $C_{22}H_{32}NJCl \cdot H_2O$ Calculated: C 50.20, H 6.51, N 2.66; Found: C 50.53, H 6.20, N 2.98.

b. A mixture of [1-methyl-3-(2,6,6-trimethyl-2-cyclohexenyl)-2(trans)-propenyl]dimethyl(2,4-dichlorobenzyl)ammonium iodide (1.0 g), silver bromide (2.0 g) and methanol (15 cc) was refluxed for 3 hours, and after the filtration of the reaction mixture, the solvent of the filtrate was distilled off under reduced pressure. The residue was recrystallized from a mixed solvent of benzene and ether to give colorless crystals (0.7 g) of [1-methyl-3-(2,6,6-trimethyl-2-cyclohexenyl)-2(trans)-propenyl]dimethyl(2,4-dichlorobenzyl)ammonium bromide, m.p. 153°–154° C.

EXAMPLE 21 a. A mixture of [1-methyl-3-(2,6,6-trimethyl-2-cyclohexenyl)-2-(trans)propenyl]dimethylamine (2.2 g), α,4-dichlorotoluene (0.8 g) and ethanol (30 cc) was refluxed for 1 hour, and thereto were added water (100 cc) and potassium iodide (5.0 g). The reaction mixture was extracted with chloroform, and the chloroform layer was dried over magnesium sulfate. The solvent was distilled off, and the residue was recrystallized from ethanol to give crystals (3.1 g) of [1-methyl-3-(2,6,6-trimethyl-2-cyclohexenyl)-2(trans)-propenyl]dimethyl(4-chlorobenzyl)ammonium iodide.

Analysis: $C_{22}H_{32}NClJ$; Calculated: C 11.23, H 13.72, N 5.96, Cl 15.09, J 54.00 Found: C 11.52, H 13.70, N 5.91, Cl 14.80, J 54.07.

b. A mixture of [1-methyl-3-(2,6,6-trimethyl-2-cyclohexenyl)-2(trans)-propenyl]dimethyl(4-chlorobenzyl)ammonium iodide (2.0 g), silver chloride (1.0 g) and absolute methanol (50 cc) was refluxed for 2 hours, and the reaction mixture was filtered. The solvent of the filtrate was distilled off to give hygroscopic colorless crystals (0.9 g) of [1-methyl-3-(2,6,6-trimethyl-2-cyclohexenyl)-2(trans)-propenyl]dimethyl(4-chlorobenzyl)ammonium chloride.

N.M.R. spectrum:

| | | |
|---|---|---|
| τ = 2.41 | (quartet) | 4H |
| τ = 3.75 − 4.70 | | 3H |
| τ = 5.05 | (singlet) | 2H |
| τ = 6.90 | (singlet) | 6H |
| τ = 8.26 | (doublet) | 3H |
| τ = 8.42 | (singlet) | 3H |
| τ = 9.10 | (singlet) | 3H |
| τ = 9.18 | (singlet) | 3H |

EXAMPLE 22

To a solution of 1-[1-methyl-3-(2,6,6-trimethyl-2-cyclohexenyl)-2(trans)-propenyl]piperidine (3.0 g) in a small amount of absolute methanol was added methyliodide (2.1 g) under cooling, and the reaction mixture was allowed to stand over night. The solvent of the reaction mixture was distilled off under reduced pressure, and the residue was dissolved in dil. hydrochloric acid. The aqueous solution was washed with ether, and then adjusted to an alkalinity by adding sodium bicarbonate. The aqueous solution was extracted with chloroform, and the chloroform layer was washed with water. After drying the chloroform layer, the solvent was distilled off under reduced pressure. The residue was dissolved in methanol and thereto was added ether, and then the mixture was allowed to stand under cooling. Precipitated crystals were gathered by filtration and recrystallized from a mixed solvent of methanol and ether to give crystals (1.3 g) of 1-methyl-1-[1-methyl-3-(2,6,6-trimethyl-2-cyclohexenyl)-2(trans)-propenyl]piperidinium iodide, m.p. 156°–158° C.

Analysis: $C_{19}H_{34}NJ$; Calculated: C 56.57, H 8.50, N 3.47, J 31.46; Found: C 56.71, H 8.80, N 3.74, J 31.50.

EXAMPLE 23

With a mixture of 4-[1-methyl-3-(2,6,6-trimethyl-2-cyclohexenyl)-2(trans)-propenyl]morpholine (8.2 g) and methyliodide (13.5 g), crystals (2.0 g) of 4-methyl-4-[1-methyl-3-(2,6,6-trimethyl-2-cyclohexenyl)-2(trans)-propenyl]morpholinium iodide, m.p. 167°–174° C, were obtained according to a similar manner to the Example 22.

Analysis: $C_{18}H_{32}NOJ$; Calculated: C 53.33, H 7.96, N 3.46, J 31.31; Found: C 53.44, H 8.22, N 3.34, J 31.05.

EXAMPLE 24

To a mixture (2.4 g) of 1-[1-methyl-3-(2,6,6-trimethyl-1-cyclohexenyl)-2(trans)-propenyl]pyrrolidine and 1-[1-methyl-3-(2,6,6-trimethyl-2-cyclohexenyl)-2(trans)-propenyl]pyrrolidine (2:1) was added methyliodide (10.0 g), and the reaction mixture was sealed and allowed to stand over night. After the completion of the reaction, water (50 cc) was added to the reaction mixture, and the mixture was washed with ether. The mixture was extracted with chloroform, and the chloroform layer was dried over magnesium sulfate. The chloroform was distilled off to give an oil (2.8 g) consisting of 1-methyl-1-[1-methyl-3-(2,6,6-trimethyl-1-cyclohexenyl)-2(trans)-propenyl]pyrrolidinium iodide and 1-methyl-1-[1-methyl-3-(2,6,6-trimethyl-2-cyclohexenyl)-2(trans)-propenyl]pyrrolidinium iodide.

Analysis: $C_{18}H_{32}NJ$; Calculated: C 55.51, H 8.29, N 3.59, J 31.61; Found: C 55.54, H 8.06, N 3.41, J 32.06.

N.M.R. spectrum:

| | | |
|---|---|---|
| τ = 9.00 | (singlet) | ⎫ |
| τ = 9.10 | (singlet) | ⎬ 6H |
| τ = 9.18 | (singlet) | ⎭ |
| τ = 8.40 | (singlet) | ⎫ |
| τ = 8.50 | (singlet) | ⎬ 6H |
| τ = 8.45 | (singlet) | ⎭ |
| τ = 7.05 | (singlet) | 3H |
| τ = 6.25 | (singlet) | 4H |
| τ = 7.22 | (singlet) | 4H |
| τ = 3.75 − 4.45 | | 2 − 3H |

EXAMPLE 25 a. A mixture (1.0 g) of [1-methyl-3-(2,6,6-trimethyl-1-cyclohexenyl)-2(trans)-propenyl]dimethylamine and [1-methyl-3-(2,6,6-trimethyl-2-cyclohexenyl)-2(trans)-propenyl]dimethylamine was added to a solution of methyliodide (1.0 g) in methanol (10 cc), and the reaction mixture was allowed to stand over night. To the reaction mixture was added ether, and precipitated crystals were gathered by filtration, and then recrystallized from benzene to give colorless crystals (1.5 g) consisting of [1-methyl-3-(2,6,6-trimethyl-1-cyclohexenyl)-2(trans)-propenyl]trimethylammonium iodide and [1-methyl-3-(2,6,6-trimethyl-2-cyclohexenyl)-2(trans)-propenyl]trimethylammonium iodide (1:1).

It was observed in the I.R. spectrum of the crystals that the absorptions at 2750 and 2800 cm-1 based on the tertiary amine, which were existing in that of the starting material, have disappeared.

Analysis: $C_{16}H_{30}NJ$; Calculated: C 52.89, H 8.32, N 3.85; Found: C 52.79, H 8.41, N 3.84.

N.M.R. spectrum:

| | | |
|---|---|---|
| τ = 9.16 | (singlet) | ⎫ |
| τ = 9.10 | (singlet) | ⎬ 6H |
| τ = 9.00 | (singlet) | ⎭ |
| τ = 8.44 | (multiplet) | 6H |
| τ = 6.63 | (singlet) | 9H |
| τ = 5.40 | (multiplet) | 1H |
| τ = 3.7 − 4.72 | | 3H | b. A mixture (0.5 g) of [1-methyl-3-(2,6,6-trimethyl-1-cyclohexenyl)-2(trans)-propenyl]trimethylammonium iodide and [1-methyl-3-(2,6,6-trimethyl-2-cyclohexenyl)-2(trans)-propenyl]trimethylammonium iodide (1:1) was added to a solution of silver chloride (1.0 g) in absolute methanol (30 cc), and the mixture was refluxed for 5 hours. After the filtration of the reaction mixture, the solvent of the filtrate was distilled off under reduced pressure to give hygroscopic, colorless crystals (0.3 g) consisting of [1-methyl-3-(2,6,6-trimethyl-1-cyclohexenyl)-2(trans)-propenyl]trimethylammonium chloride and [1-methyl-3-(2,6,6-trimethyl-2-cyclohexenyl)-2(trans)-propenyl]trimethylammonium chloride (1:1).

N.M.R. spectrum:

| | | |
|---|---|---|
| τ = 9.15 | (singlet) | ⎫ |
| τ = 9.10 | (singlet) | ⎬ 6H |
| τ = 9.08 | (singlet) | ⎭ |
| τ = 8.44 | (multiplet) | 6H |
| τ = 6.60 | (singlet) | 9H |
| τ = 5.40 | (multiplet) | 1H |
| τ = 3.80 − 4.80 | | 3H |

EXAMPLE 26

A mixture (5.0 g) of [1-methyl-3-(2,6,6-trimethyl-1-cyclohexenyl)-2(trans)-propenyl]dimethylamine and [1-methyl-3-(2,6,6-trimethyl-2-cyclohexenyl)-2(trans)-propenyl]dimethyamine (1:1) was added to a solution of α,3,4-trichlorotoluene (3.0 g) in 99 % ethanol (30 cc), and the mixture was sealed. The sealed reaction mixture was heated for 5 hours at 100° C, and then the reaction mixture was adjusted to acidity by adding dil. hydrochloric acid, and washed with ether. The reaction mixture was further adjusted to alkalinity by adding dil. aqueous solution of sodium hydroxide, and extracted with ether. The ether layer was concentrated to dryness, and to the residue were added water (100 cc) and potassium iodide (10.0 g). The mixture was extracted with chloroform, the chloroform layer was dried. The chloroform was distilled off, and then the residue was allowed to stand for 3 days. Precipitated crystals were recrystallized from methanol to give yellowish crystals (4.2 g) consisting of [1-methyl-3-(2,6,6-trimethyl-1-cyclohexenyl)-2(trans)-propenyl]-dimethyl(3,4-dichlorobenzyl)ammonium iodide and [1-methyl-3-(2,6,6-trimethyl-2-cyclohexenyl)-2(trans)-propenyl]dimethyl(3,4-dichlorobenzyl)ammonium iodide (1:1).

It was observed in the I.R. spectrum of the crystals that the absorptions at 2750 and 2800 cm-1 based on the tertiary amine, which were existing in that of the starting material, have disappeared.

Analysis: $C_{22}H_{32}NClJ.H_2O$; Calculated: C 50.20, H 6.51, N 2.66; Found: C 49.92, H 6.80, N 2.46.

| N.M.R. spectrum: | | |
|---|---|---|
| τ = 9.21 | (singlet) | 3H |
| τ = 9.21 | (singlet) | 3H |
| τ = 8.98 | (singlet) | |
| τ = 8.42 | (singlet) | 3H |
| τ = 8.26 | (doublet) | 3H |
| τ = 6.87 | (singlet) | 6H |
| τ = 5.20 | (multiplet) | 1H |
| τ = 4.84 | (singlet) | 2H |
| τ = 3.75 – 4.65 | | |
| τ = 2.51 | (doublet) | 1H |
| τ = 2.16 | (doublet) | 1H |
| τ = 2.00 | (doublet) | 1H |

EXAMPLE 27

A mixture (5.0 g) of [1-methyl-3-(2,6,6-trimethyl-1-cyclohexenyl-2(trans)-propenyl]dimethylamine and [1-methyl-3-(2,6,6-trimethyl-2-cyclohexenyl)-2(trans)-propenyl]dimethylamine was added to a solution of α,2,4-trichlorotoluene (2.4 g) in 99 % ethanol (30 cc), and the reaction mixture was sealed and heated at 100° C for 10 hours. After adjusting the mixture to an acidity by adding dil. hydrochloric acid, the reaction mixture was washed with ether, and alkalized. The mixture was extracted with ether, and the solvent of the ether layer was distilled off. To the residue was added water (100 cc), and then potassium iodide (20.0 g) was further added thereto. The aqueous solution was extracted with chloroform, the chloroform layer was washed with a saturated aqueous solution of sodium thiosulfate, and dried. The chloroform was distilled off, and the residue was recrystallized from methanol to give crystals (4.2 g) consisting of [1-methyl-3-(2,6,6-trimethyl-2-cyclohexenyl)-2(trans)-propenyl]dimethyl(2,4-dichlorobenzyl)ammonium iodide and [1-methyl-3-(2,6,6-trimethyl-1-cyclohexenyl)-2(trans)-propenyl]dimethyl(2,4-dichlorobenzyl)ammonium iodide.

It was observed in the I.R. spectrum of the above crystals that the absorptions at 2750 and 2800 cm-1 based on the tertiary amine, which were existing in that of the starting material, have disappeared.

Analysis: $C_{22}H_{32}NClJ$; Calculated: C 51.98, H 6.35, N 2.76; Found: C 52.11, H 6.62, N 2.71.

| N.M.R. spectrum: | | |
|---|---|---|
| τ = 9.12 | (singlet) | 3H |
| τ = 9.09 | (singlet) | 3H |
| τ = 8.95 | (singlet) | |
| τ = 8.40 | (multiplet) | 3H |
| τ = 8.25 | (doublet) | 3H |
| τ = 6.89 | (singlet) | 3H |
| τ = 6.82 | (singlet) | 3H |
| τ = 6.55 | (multiplet) | |
| τ = 5.00 | (singlet) | 2H |
| τ = 3.55 – 4.65 | (multiplet) | 3H |
| τ = 2.60 | (doublet) | 1H |
| τ = 2.48 | (doublet) | 1H |
| τ = 1.89 | (doublet) | 1H |

EXAMPLE 28

A solution of [1-methyl-3-(2,6,6-trimethyl-2-cyclohexenyl)-2 (trans)-propenyl]dimethylamine (2.0 g) and 3-propenylbromide (1.5 g) in methanol (30 cc) was refluxed for 3 hours, and the solvent of the reaction mixture was distilled off. To the residue was added water (50 cc), and the aqueous solution was washed with ether and potassium iodide (1.0 g) was added thereto. The reaction mixture was allowed to stand for 1 hour and extracted with chloroform. The chloroform layer was dried and the chloroform was distilled off. The residue was dissolved in benzene, and thereto was added ether. Precipitated crystals were gathered by filtration and dried to give yellowish crystals (3.5 g) of [1-methyl-3-(2,6,6-trimethyl-2-cyclohexenyl)-2(trans)-propenyl]dimethyl(2-propenyl)ammonium iodide.

Analysis: $C_{17}H_{32}NJ$; Calculated: C 55.53, H 8.28, N 3.60; Found: C 55.35, H 8.18, N 3.57.

EXAMPLE 29

A solution of [1-methyl-3-(2,6,6-trimethyl-2-cyclohexenyl)-2(trans)-propenyl]dimethylamine (2.0 g) and 2-chloroethanol (1.0 g) in ethanol (50 cc) was refluxed for 8 hours, and the solvent of the reaction mixture was distilled off. The residue was dissolved in water (50 cc), and the aqueous solution was washed with ether. Thereto was added potassium iodide (1.0 g), and the mixture was allowed to stand for 1 hour. The mixture was extractd with chloroform, and the chloroform layer was washed with a saturated aqueous solution of sodium thiosulfate and dried. The solvent was distilled off, and the residue was recrystallized from benzene to give yellowish crystals 2.7 g) of [1-methyl-3-(2,6,6-trimethyl-2-cyclohexenyl-2(trans)-propenyl]dimethyl(2-hydroxyethyl)ammonium iodide.

Analysis: $C_{17}H_{32}NOJ$; Calculated: C 51.91, H 82 0, N 3.56; Found: C 51.78, G 8.38, N 3.53.

EXAMPLE 30

A solution of [1-methyl-3-(2,6,6-trimethyl-2-cyclohexenyl)-2(trans)-propenyl]dimethylamine (2.0 g) and 2-chloropropionic acid (0.5 g) in methanol (50 cc) was refluxed for 8 hours on a water-bath, and the solvent of the reaction mixture was distilled off. The residue was dissolved in water, and the aqueous solution was washed with ether. Potassium iodide (3 g) was added thereto, and the mixture was extracted with chloroform. The chloroform of the extract was distilled off, and the residue was recrystallized from a mixed solvent of benzene and methanol to give crystals (2.1 g) of [1-methyl-3-(2,6,6-trimethyl-2-cyclohexenyl)-2(trans)-propenyl]dimethyl(2-carboxyethyl)ammonium iodide.

Analysis: $C_{18}H_{32}NO_2J$; Calculated: C 51.31, H 7.66, N 3.32, J 30.12; Found: C 51.03, H 8.06, N 3.10, J 30.70.

EXAMPLE 31

A solution of [1-methyl-3-(2,6,6-trimethyl-2-cyclohexenyl)-2(trans)-propenyl]dimethylamine (2.2 g) and allyl chloroacetate (1.1 g) ethanol (50 cc) was refluxed for 2 hours, and the solvent of the reaction mixture was distilled off. The residue was dissolved in water (100 cc), and potassium iodide (5.0 g) was added thereto. The aqueous solution was extracted with chloroform, and the chloroform layer was dried. The chloroform was distilled off to give a yellowish oil (3.4 g) of [1-methyl-3-(2,6,6-trimethyl-2-cyclohexenyl)-2(trans)-propenyl]dimethyl(allkyloxycarbonylmethyl)ammonium iodide.

It was observed in the I.R. spectrum of this oil that the absorptions at 2750 and 2800 cm-1 based on the tertiary amine, which were existing in that of the starting material, have disappeared.

EXAMPLE 32

A solution of [1-methyl-3-(2,6,6-trimethylcyclohexyl)propyl]dimethylamine (3.0 g) and propargylbromide (3.0 g) in methanol (20 cc) was refluxed for 1 hour, and thereto was added a solution of potassium iodide (4.5 g) in water (15 cc). After shaking the mixture, water (50 cc) was added thereto, and the aqueous solution was extracted with chloroform, The chloroform layer was washed with water, dried and concentrated to dryness. The residue was recrystallized from a mixed solvent of ethanol and ether to give colorless crystals (4.5 g) of [1-methyl-3-(2,6,6-trimethylcyclohexyl)propyl]dimethylpropargylammonium iodide, m.p. 165°–167° C.

EXAMPLE 33

A solution of [3-(2,6,6-trimethyl-1-cyclohexenyl)-2(trans)-propenyl]dimethylamine (2.0 g) and propargylbromide (2.0 g) in methanol (20 cc) was refluxed for 1 hour, and concentrated. To the residue was added water, and the aqueous solution was washed with ether and extracted with chloroform. The chloroform layer was dried and concentrated to dryness to give an oil (2.9 g) of [3-(2,6,6-trimethyl-1-cyclohexenyl)-2(trans)-propenyl]dimethylpropargylammonium bromide.

It was observed in the I.R. spectrum of this oil that the absorptions at 2750 and 2800 cm-1 based on the tertiary amine, which were existing in that of the starting material, have disappeared.

EXAMPLE 34 a. A solution of [1-methyl-3-(2,6,6-trimethyl-2-cyclohexenyl)-2(trans)-propenyl]dimethylamine (5.0 g) and 1,2-ethyldibromide (50 g) in absolute methanol (2 cc) was heated at 70°–80° C for 8 hours, and the excess 1,2-ethyldibromide was distilled off completely azeotropically by adding benzene. The residue was recrystallized from a mixed solvent of acetonitrile and ether to give humid crystals (5.9 g) of [1-methyl-3-(2,6,6-trimethyl-2-cyclohexenyl)-2(trans)-propenyl]dimethyl(2bromoethyl)ammonium bromide.

| N.M.R. spectrum: | | |
|---|---|---|
| $\tau = 9.10 - 9.17$ | (multiplet) | 6H |
| $\tau = 8.37 - 8.47$ | (multiplet) | 7H |
| $\tau = 7.75 - 8.17$ | (multiplet) | 4H |
| $\tau = 6.60$ | (doublet) | 6H |
| $\tau = 5.98$ | (singlet) | 4H |
| $\tau = 4.28 - 4.70$ | (multiplet) | 3H | b. A solution of [1-methyl-3-(2,6,6-trimethyl-2-cyclohexenyl)-2(trans)-propenyl]dimethyl(2-bromoethyl)ammonium bromide (1 g) and potassium iodide (0.54 g) in a mixed solvent of ethanol (5 cc) and water (5 cc) was stirred for 30 minutes at room temperature, and the reaction mixture was concentrated under reduced pressure. The residue was extracted with chloroform, and the solvent of the chloroform layer was distilled off. To the residue was added benzene, and the benzene layer was concentrated to dryness. The residue was recrystallized from a mixed solvent of acetonitrile and ether to give orange crystals (1.0 g) of [1-methyl-3-(2,6,6-trimethyl-2-cyclohexenyl)-2(trans)-propenyl]dimethyl(2-bromoethyl)ammonium iodide, m.p. 149°–151° C.

EXAMPLE 35

To a solution of [2-(3,3,5-trimethylcyclohexyl)ethyl]dimethylamine (1.0 g) in benzene (30 cc) was added methyliodide (2.0 g), and the mixture was allowed to stand over night. Precipitated crystals were gathered by filtration and recrystallized from a mixed solvent of benzene and ether to give colorless crystals (1.6 g) of [2-(3,3,5-trimethylcyclohexyl)ethyl]trimethylammonium iodide, m.p. 263°–265° C.

Analysis: $C_{14}H_{30}NJ$;
Calculated: C 49.56, H 8.91, N 4.13, J 37.40; Found: C 49.47, H 8.89, N 4.18, J 37.61.

EXAMPLE 36

With a mixture of [2-(3,3,5-trimethylcyclohexyl)ethyl]dimethylamine (1.0 g), benzene (30 cc) and ethyliodide (4.0 g), colorless crystals (1.3 g) of [2-(3,3,5-trimethylcyclohexyl)ethyl]dimethylethylammonium iodide, m.p. 200°–202° C, were obtained according to a similar manner to the preceding Example 35.

Analysis: $C_{15}H_{32}NJ$; Calculated: C 50.99, H 9.13, N 3.96, J 35.92; Found: C 51.26, H 9.08, N 3.91, J 35.68.

EXAMPLE 37

A mixture of [2-(3,3,5-trimethylcyclohexyl)ethyl]dimethylamine (1.0 g), 1-heptylchloride (5.0 g) and absolute ethanol was refluxed for 7 hours, and then the solvent of the reaction mixture was distilled off under reduced pressure. To the residue was added a solution of potassium iodide (4.0 g) in a mixed solvent of ethanol (15 cc) and water (10 cc), and water was added to the mixture. The aqueous solution was extracted with chloroform, and the chloroform layer was washed with water, dried and the solvent was distilled off. The residue was recrystallized from a mixed solvent of ethanol and ether to give colorless crystals (1.2 g) of [2-(3,3,5- trimethylcyclohexyl)ethyl]dimethylheptylammonium iodide, m.p. 110°–112° C.

Analysis: $C_{20}H_{42}NJ$; Calculated: C 56.72, H 10.00, N 3.31, J 29.97; Found: C 56.53, H 9.96, N 3.15, J 30.15.

EXAMPLE 38

To a solution of [2-(3,3,5-trimethylcyclohexyl)ethyl]dimethylamine (1.0 g) in benzene (30 cc) was added propargylbromide (5.0 g), and the reaction mixture was allowed to stand over night. The solvent was distilled off, and a solution of potassium iodide (4.0 g) in a mixed solvent of ethanol (15 cc) and water (10 cc) was added to the residue. Water (50 cc) was added to the reaction mixture and the aqueous solution was extracted with chloroform. The chloroform layer was washed with water, dried and the solvent was distilled off to give a yellowish oil (1.2 g) of [2-(3,3,5-trimethylcyclohexyl)ethyl]dimethylpropargylammonium iodide.

I.R. spectrum: 2200 cm-1 (C≡C)

It was observed in the I.R. spectrum of this oil that the absorptions at 2750 and 2800 cm-1 based on the tertiary amine, which were existing in that of the starting material, have disappeared.

The composition of the invention may contain other ingredients, for example, protective colloids such as gelatin, glue, casein, gums and polyvinyl alcohol; sodium polyphosphates; cellulose ethers, stabilisers such as ethylene diamine tetraacetic acid; other herbicides or pesticides; and stickers, for example, non-volatile oils.

The composition of the invention can be used in any conventionally known manner. The most suitable method of use, however, should be selected depending on the object of use, the type of plants to be treated and the period of application. Illustrative methods of application of the composition are spraying or dusting of the composition to the surfaces of leaves or/and leafstalks of plants, treatment of soil on which plants grow with the composition, spraying of the composition onto seeds, fruits, tubers, etc., soaking of seeds, fruits, tubers, etc., into the composition.

The compositions of the invention may be formulated as wettable powders, dusts, granules, solution, emulsifiable concentrates, emulsions and pasters.

Solid preparations can be prepared with inert powders to the compound [I]. The preparations thus can be homogeneous powders that either can be used as such, diluted with inert solids to form dusts, or suspended in a suitable liquid medium for spray application. The powders usually comprise the active ingredient admixed with suitable amounts of conditioning agents. Natural clays, either absorptive such as attapulgite or relatively non-absorptive such as china clays, diatomaceous earth, synthetic fine silica, calcium silicate and other inert solid carriers can be used. The active ingredient usually makes up from about 1 to about 80% by weight, preferably from about 1 to about 50% by weight, of these powder preparations. For conversion of the powders to dusts, talc, pyrophyllite, volcanic ash and other dense, lactose, sodium chloride, rapid-settling inert solids customarily are used.

Liquid preparations including the active ingredient can be prepared by admixing the same with a suitable liquid medium. The active ingredient can be either in solution or in suspension in the liquid medium. Typical of the liquid media commonly employed are water, kerosene, Stoddard solvent, xylene, alcohols, alkylated naphthalene, glycols and ketones such as diiosbutylketone, cyclohexanone, etc. The active ingredient usually makes up from about 1 to about 80% by weight, preferably from about 1 to about 50% by weight, of these liquid preparations. Some of these preparations are designed to be used as such, and others to be extended with large quantities of water.

Preparations in the form of wettable powders or liquids can also include one or more surface active agents such as wetting, spreading, dispersing or emulsifying agent. Thus mixtures of the above liquids with the active ingredient can contain an emulsifying agent to make an emulsifiable oil preparation. The surface active agents cause the compositions of the liquid or dry to disperse or emulsify easily in water to give aqueous sprays. The surface active agents employed can be of the anionic, cationic and/or non-ionic type.

EXAMPLES FOR THE PREPARATION OF COMPOSITION

Practical and preferred embodiments of the compositions are illustrated in the following Examples wherein parts are by weight.

EXAMPLE 1

| | |
|---|---|
| [3-Methyl-5-(2,6,6-trimethyl-1-cyclohexenyl)-2,4-pentadienyl]trimethylammonium iodide | 95 parts |
| Polyoxyethylenealkylallylether | 5 parts |

The above mixture is diluted with water to a desired concentration when it is used.

EXAMPLE 2

| | |
|---|---|
| [1-Methyl-3-(2,6,6-trimethyl-2-cyclohexenyl)-2-propenyl]trimethylammonium iodide | 10 parts |
| Tween 20 (trade name) | 1 part |
| Ethanol | 89 parts |

The above mixture is diluted with water to a desired concentration when it is used.

EXAMPLE 3

| | |
|---|---|
| [1-Methyl-3-(2,6,6-trimethyl-1-cyclohexenyl)propyl]-trimethylammonium iodide | 20 parts |
| Sodium ligninsulfonate | 2 parts |
| Polyoxyethylenealkylallylether | 2 parts |
| Clay | 76 parts |

The above mixture is diluted with water to a desired concentration when it is used.

EXAMPLE 4

| | |
|---|---|
| [1-Methyl-3-(2,6,6,-trimethyl-2-cyclohexenyl)-2-propenyl]dimethyl(2,4-dichlorobenzyl)ammonium iodide | 20 parts |

-continued

| Polyoxyethylenealkylallylether | 10 parts |
| --- | --- |
| Toluene | 70 parts |

The above mixture is diluted with water to a desired concentration when it is used.

EXAMPLE 5

| [1-Methyl-3-(2,6,6-trimethylcyclohexyl)propyl]-trimethylammonium iodide | 2 parts |
| --- | --- |
| Talc | 98 parts |

The above mixture is diluted with water to a desired concentration when it is used.

EXAMPLE 6

| [1-Methyl-3-(2,6,6-trimethyl-1-cyclohexenyl)-2-propenyl]trimethylammonium iodide | 10 parts |
| --- | --- |

-continued

| Water | 90 parts |
| --- | --- |

The above mixture is diluted with water to a desired concentration when it is used.

EXAMPLE 7

| [1-Methyl-3-(2,6,6-trimethyl-1-cyclohexenyl)-2-propenyl]trimethylammonium iodide | 10 parts |
| --- | --- |
| Lactose or NaCl | 90 parts |

The above mixture is prepared into tablets.

What is claimed as new and intended to be covered by Letters Patent is:

1. A quaternary ammonium salt of the formula

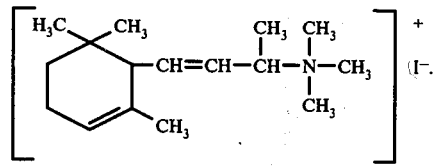

* * * * *